United States Patent [19]

Noda et al.

[11] 4,455,146

[45] Jun. 19, 1984

[54] NOVEL PLASTERS

[75] Inventors: Kanji Noda, Chikushino; Akira Nakagawa, Tosu; Tetsuya Yamagata, Tosu; Masasi Kobayasi, Tosu; Tadayoshi Suenaga, Mine; Fumiaki Tokubuchi, Tosu; Kazuki Noguchi, Ogohri; Tadaaki Yoshitake; Masayoshi Tsuji, both of Tosu; Hiroyuki Ide, Fukuoka, all of Japan

[73] Assignee: Hisamitsu Pharmaceutical Co., Ltd., Saga, Japan

[21] Appl. No.: 354,114

[22] Filed: Mar. 2, 1982

Related U.S. Application Data

[63] Continuation-in-part of Ser. No. 123,616, Feb. 22, 1980, abandoned.

[30] Foreign Application Priority Data

Apr. 3, 1979 [JP] Japan .................. 54-40787
Apr. 19, 1979 [JP] Japan .................. 54-49263

[51] Int. Cl.$^3$ ............................................. A61F 7/02
[52] U.S. Cl. .................................... 604/897; 128/156; 156/231; 156/246; 156/247; 156/249; 156/289; 156/334; 424/27; 424/28; 424/78; 424/83; 428/349; 428/352; 428/354; 428/355; 604/290; 604/304; 604/896

[58] Field of Search .............. 128/156; 604/304, 303, 604/290, 293, 896, 897; 424/27, 28, 78, 83; 524/300; 428/355, 349, 354, 352, 521; 156/247, 249, 289, 231, 334, 246

[56] References Cited

U.S. PATENT DOCUMENTS

| 3,598,123 | 8/1971 | Zaffaroni | 128/156 |
| 3,699,963 | 10/1972 | Zaffaroni | 604/304 |
| 3,731,683 | 5/1973 | Zaffaroni | 604/304 |
| 3,742,951 | 7/1973 | Zaffaroni | 604/304 |
| 4,147,831 | 4/1979 | Balinth | 128/156 |
| 4,153,055 | 5/1979 | Etes | 128/156 |
| 4,166,706 | 9/1979 | Korpman | 428/355 |

FOREIGN PATENT DOCUMENTS

| 54-138124 | 10/1979 | Japan | 424/28 |
| 55-20726 | 2/1980 | Japan | 424/28 |
| 55-92314 | 7/1980 | Japan | 424/28 |
| 952522 | 3/1964 | United Kingdom | 428/447 |

*Primary Examiner*—Ellis P. Robinson
*Attorney, Agent, or Firm*—Jordan and Hamburg

[57] ABSTRACT

A novel plaster comprising a thermoplastic elastomer, an oil or higher fatty acid, a tack-providing resin and a medicinal ingredient. The plaster may be easily released therefrom without giving appreciable irritation or pain to the skin and body hairs of human bodies after applied thereto, while it may nevertheless exhibit satisfactory tackiness and adhesive strength when applied to human bodies.

11 Claims, 4 Drawing Figures

Percutaneous absorption of Etofenamate in men after topical application of plasters.

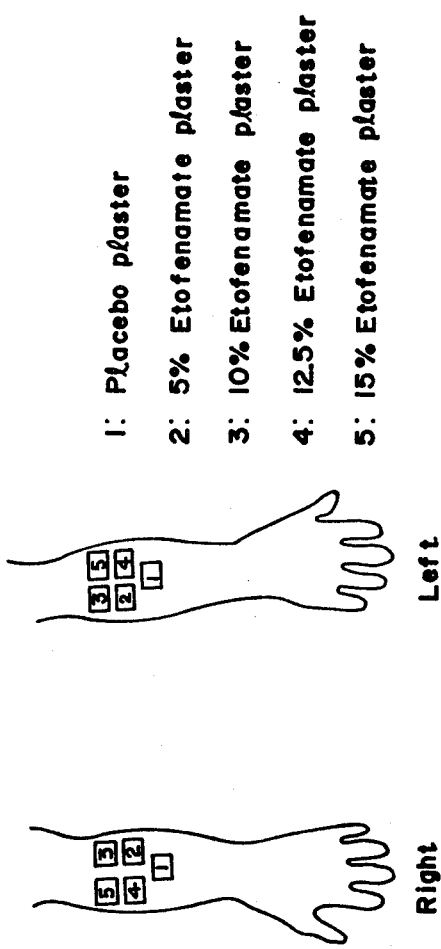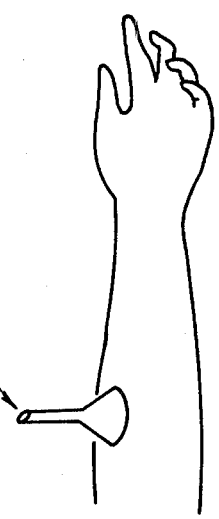

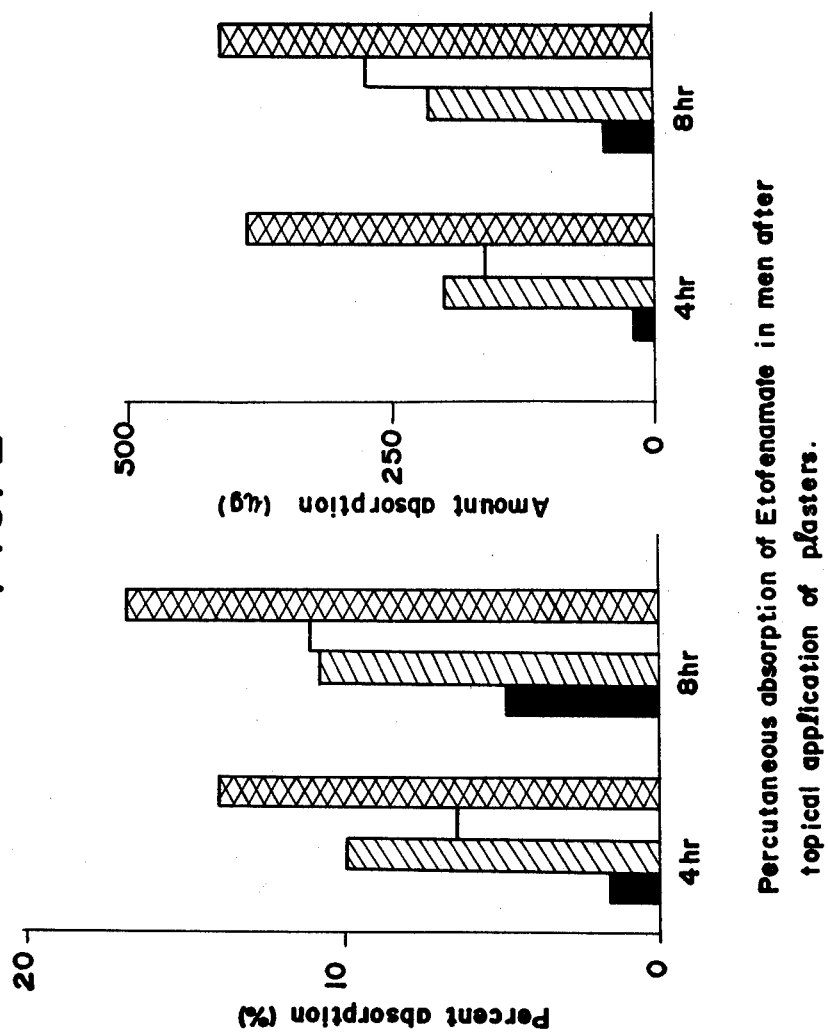

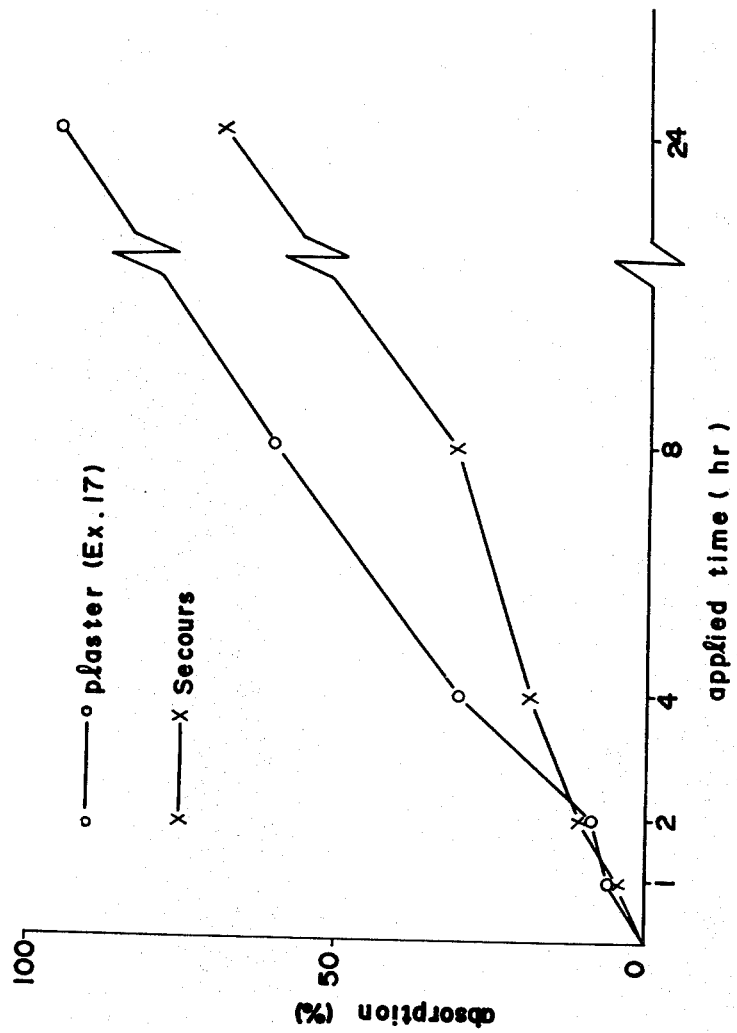

NOVEL PLASTERS

This is a Continuation-in-Part application to Ser. No. 123,616 filed Feb. 22, 1980, now abandoned.

This invention relates to plasters which comprise a thermoplastic elastomer and are adapted to be applied directly to the inflammatory part of human skin or the like.

The base ingredients of conventional plasters, which have heretofore been generally known, are those containing such rubber or acrylic tackifier as used in adhesive plasters.

However, the conventional plasters are excellent in tackiness and adhesiveness when applied to the skin, while they are disadvantageous in that the applied plasters will pull the body hair because of their high adhesive strength when peeled off the skin or will sometimes physically injure the skin or produce rash thereon. Thus, there have widely been sought novel plasters which will retain their high tackiness and adhesiveness when applied to the skin and will give little irritation to the body hair and skin when peeled or removed therefrom.

Pains suffered at the time of peeling plasters are typically due to affinity between the skin surface and a medicine applied thereto, inflow of the medicine into the undulated portions of the skin surface and anchoring effects by covering the body hair with the plaster.

Since a plaster to be prepared using therein an acrylic polymer as the one-component base is intended to be made balanced in properties by selecting the polymerization degree of the polymer to be used, it cannot be intended to be done so by varying the composition of a multi-component base as in a plaster to be prepared using the multi-component base. Thus, the former plaster will naturally take a rigid, less elastic and small form and it will therefore give a greater pain when peeled. Further, even a plaster prepared using natural rubber as the base has the same drawback as the plaster prepared using the acrylic polymer and raises a problem as to its value in practical use since flow of the medicine and separation of the mixed components are aggravated. There has now been generally known a mixing technique which comprises chemical bridging of rubber as measures for preventing said flow and separation, however, the mixing technique is not feasible since it is difficult to obtain plasters in a fixed stable quality by the use of said technique and it requires a great expense to set up equipment for carrying out the technique. Furthermore, plasters prepared using the acrylic polymer or natural rubber are those which have been produced through several processes; thus, they have raised problems as to their cost, operational environments and the like.

In an attempt to obtain plasters which meet said requirements and are excellent in stability, dischargeability of the medicine and medicinal efficacy, the present inventors made various studies and experiments and, as a result of their studies, found that a thermoplastic elastomer is dissolved in an oil or higher fatty acid and mixed with a tack-providing resin and a medicinal ingredient, after which the whole is spread under heat in the sheet form on a support to obtain a plaster. The plasters so obtained are excellent in tackiness, adhesiveness, easiness of peeling and other physical stability as well as in dischargeability of the medicine and pharmacological effects, cause very few side reactions such as formation of a rash when applied, raise no problems as to operational hygiene and may be produced as an anti-inflammatory analgesic plaster at a low cost in a short time. This invention is based on this finding.

The novel plaster of this invention is prepared by incorporating a medicinal ingredient in a "base material" comprising a thermoplastic elastomer, an oil or higher fatty acid and a tack-providing resin, while adjusting the tackiness and adhesive strength of the resulting plaster as desired.

As an example of plaster comprising a thermoplastic elastomer as the base material, an adhesive composition using therein only an A-B-A type block copolymer has already been disclosed by Japanese Pat. Appln. Laying-Open Gazette No. 17037/69; as is apparent from the Gazette, however, the adhesive composition is useful only for producing pressure sensitive tapes (such as masking tapes), adhesive sheets, primers for other adhesives, adhesive tapes, meding tapes, electrical insulation tapes, laminates, hot-melt adhesives, mastics, cement, caulking compounds, binders, sealants, other pressure sensitive adhesives, delayed tack adhesives, adhesive latices, shoe sole adhesives, cloth backings, carpet backings and the like. Further, said Gazette does not disclose anything about the use of the adhesive composition for medicinal purposes and it neither disclose nor even suggest about anything about the use thereof as plasters.

The ingredients or components of the plaster of this invention will be explained hereinunder in more detail.

BRIEF DESCRIPTION OF THE DRAWINGS

FIG. 1A is a view showing plaster-applied cites on both forearms as described in Experiment 8.

FIG. 1B shows the use of a funnel for washing the plaster on the skin surface at the applied cite.

FIG. 2 is a graph showing percutaneous absorption of etofenamate.

FIG. 3 is a graph showing the effect of adhesive mass (base) in percutaneous absorption

Figure 4:
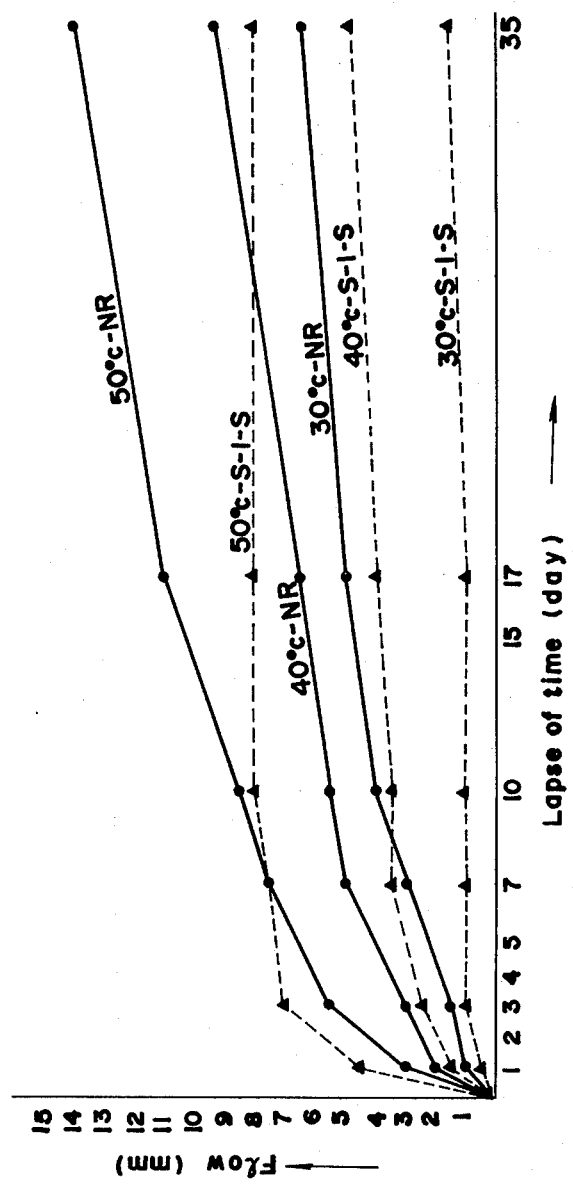
FIG. 4 is a graph showing laspe of time and flow.

The thermoplastic elastomer which is a main ingredient of the base material of the plaster of this invention, is a block copolymer represented by the following general formula

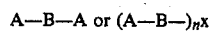

wherein A is substantially a monovinyl-substituted aromatic compound polymer block, B is a substantially conjugated diolefin polymer block, n is an integer of from 3 to 7, and X indicates a residue derived from a polyfunctional compound with which 3-7 (n) polymer chains (A-B) are combined. More particularly, the block copolymer of the formula represents a TR block copolymer, a radial TR block copolymer or a mixture thereof.

The above monovinyl-substituted aromatic compounds include styrene, o- or p-vinyltoluene, methylstyrene and ethylstyrene. The conjugated diolefins include 1,3-butadiene, 1,3-pentadiene and isoprene. A combination of styrene with 1,3-butadiene, and a combination of styrene with isoprene are particularly preferable combinations. The block A which is a polymer of styrene, is a non-elastomeric thermoplastic rigid polymer having a glass transition temperature of not lower than room temperature; the block B which is a polymer of isoprene or butadiene, is an elastomeric polymer having a glass transition temperature lower than room temperature.

The end block A in the above block copolymer is contained therein in an amount of 10–50% by weight of the block copolymer.

The oils or higher fatty acids used as one of the ingredients of the plaster of this invention will then be detailed hereinbelow.

The oils and higher fatty acids useful in the practice of this invention must be a solvent for the block B but they must not be a solvent for the block A. The solvents for the block B include almond oil, olive oil, camellia oil, persic oil, peanut oil, sesame oil, soybean oil, mink oil, cotton seed oil, corn oil, safflower oil, coconut oil, castor oil, oleic acid and liquid paraffin, among which are preferred almond oil, olive oil, camellia oil, persic oil, peanut oil, oleic acid, liquid paraffin and the like.

The plaster of this invention has quite satisfactory properties as such as previously mentioned and, to this end, it is necessary to add a tack-providing resin to the prevously mentioned ingredients. The tack-providing agents include rosin, dehydrogenated rosin, glycerine esters of dehydrogenated rosin, glycerine esters of gun rosin, hydrogenated rosin, glycerine esters of hydrogenated rosin, pentaerithritol esters of hydrogenated rosin, methyl esters of hydrogenated rosin, polymerized rosin, glycerine esters of polymerized rosin, coumarone-indene resins, hydrogenated petroleum resins, maleic anhydride-modified rosin and rosin derivatives, $C_5$ petroleum resins and half esters of styrenemaleic acid compolymers. These tack-providing agents may suitably be used alone or in combination depending on the tackiness and adhesive strength required on the part to which the resulting plaster is to be applied.

The compounds used as medicinal ingredients in this invention include methyl salicylate, glycol salicylate such as ethylene glycol salicylate, salicylic acid, menthol, peppermint oil, camphor, thymol, acrinol, scopolia extract, chlorpheniramine maleate, diphenhydramine, benzyl nicotinate, capsicum extract, nonyl vanillylamide, capsaicin, ibuprofen, indomethacin, alclofenac, ketoprofen, flurbiprofen, fenoprofen, flufenamic acid, niflumic acid, indoprofen, Voltaren (diclofenac sodium), naproxen, clidanac, tolmetin, suprofen, bendazac, oxepinac, pranoprofen, benoxaprofen, piroxican, fentiazac esters thereof such as etofenamate and corticosteroids. These medicinal compounds may be used alone or in combination.

Steroids which may be used herein include cortisone-21-acetate, hydrocortisone, hydrocortisone-21-acetate, hydrocortisone-21-caproate, prednisone, prednisolone, prednisoline-21-acetate, 6-methyl-prednisolone, methyl-prednisolone acetate, triamcinolone-16α, 17α-acetonide, dexamethasone, dexamethasone-21-acetate, dexamethasone-21-disodium salt phosphate, betamethasone-17-valerate, flurandrenolone-16α, 17α-acetonide, fluocinolone-16α, 17α-acetonide, beclomethasone-17α, 21-dipropionate, flumethasone-21-pivalate, halcinonide, betamethasone-17,21-dipropionate, betamethasone-17-benzoate, clobetasol propionate, 17α-desoxy methasone and difluotolone.

As required, the plasters of this invention may be incorporated with additives and fillers, such as an antiaging agent (age resistor), antioxidant and reinforcing filler, without destroying gel-like properties.

The ingredients of the base material and the medicinal ingredient necessary to form the plaster of this invention may be blended together in their respective amounts as indicated below.

The oil or higher fatty acid may be contained in the plaster of this invention in an amount by weight of 25-370 parts per 100 parts by weight of the thermoplastic elastomer. The use of more than 370 parts by weight of the oil or fatty acid will make it difficult for the base material (this being defined as comprising the thermoplastic elastomer, oil or higher fatty acid and tack-providing resin as previously mentioned) to retain its gel-like properties and will deteriorate the base material in stability, while the use of less than 50 parts by weight thereof will make the base material strengthened in gel-like properties whereby the resulting plaster is very likely to peel from the body even if it is applied thereto, this being disadvantageous. Thus, the amount of the oil or higher fatty acid added is in the range of preferably 50-250, mor preferably 75-200, parts by weight.

The tack-providing resin may be contained in the plaster of this invention in an amount of 25-200 parts by weight per 100 parts by weight of the thermoplastic elastomer. The use of more than 200 parts by weight of the tack-providing resin will deteriorate the base material in gel-like properties whereby the users feel very painful when the resulting plaster is peeled from the body, while the use of less than 25 parts of the tack-providing resin will make it difficult to apply the resulting plaster to the body and will soon peel therefrom even if it could be applied, this being undesirable. Thus, the amount of the tack-providing resin used is in the range of preferably 50-175, more preferably 50-150, parts by weight.

The medicinal ingredient may be used in an amount of 0.09-110, preferably 0.1-90, parts by weight per 100 parts by weights of the thermoplastic elastomer.

The plaster of this invention may be prepared as follows. A mixture containing a thermoplastic elastomer, an oil or higher fatty acid and a tack-providing resin in a predetermined mixing ratio, is heated under agitation in a nitrogen gas stream to obtain a melt. The heating is effected at a temperature of 120°-200° C. and the agitation effected for 30-60 minutes. The melt so obtained was cooled to less than 130° C. and then incorporated with a medicinal ingredient. The resulting mixture was mixed for 10-20 minutes to obtain a uniform medicine-containing melt. The thus obtained medicine-containing melt was spread and coated on a support or substrate by the use of a doctor roll, reverseroll coater, slot die coater, knife coater or the like thereby to obtain the plaster. The support may suitably be selected from non-woven clothes, non-woven paper and synthetic resin films. A releasable cover is applied to the medicine-containing melt spread and coated on the support. The releasable cover may suitably be selected from releasable paper, Cellophane and plastic films such as polyethylene and polypropylene films.

In a case where a support to be used is a thermally and dimensionally unstable one, the medicine-containing melt is firstly applied to a thermally and dimensionally stable support, such as the above releasable paper, and, thereafter, the unstable support is pressed onto said melt-coated stable support to transfer the coated melt from the latter to the former thereby to obtain the plaster.

The aforementioned process for preparing the plaster is the most ideal one, however, the plaster of this invention may be obtained by any other processes using the same ingredients as in said aforementioned process.

Typical of the other processes are a process comprising dissolving the base material and the medicinal ingredient in an organic solvent, coating the resulting solution on a support and passing the solution-coated support through a drying furnace to remove the solvent and obtain a plaster and a process comprising coating a medicinal ingredient-dissolved organic solvent on an adhesive tape preliminarily coated with the base material only and then removing the organic solvent in the same manner as above thereby to obtain a plaster.

The plaster of this invention may be obtained in any shape by adjusting the thickness of the melt-dissolved solution coated. The thickness is usually in the range of $30\mu$–1 mm.

This invention will be better understood by the following examples wherein all parts are by weight unless otherwise specified.

EXAMPLE 1

One hundred (100) parts of a styrene-isoprene-styrene TR block copolymer (produced under the trademark of Cariflex TR 1107 by Shell Chemical Co.), 150 parts of liquid paraffin (produced by Wako Pure Chemical Industries Ltd.) and 50 parts of a rosin-modified maleic resin (produced under the trademark of Malkyd 2-N by Arakawa Chemical Co., Ltd.), were heated to 140°–150° C. thereby to obtain a melt. The thus obtained melt (about 150° C.) was cooled to about 120° C., incorporated with 30 parts of methyl salicylate and 21 parts of l-menthol and then mixed together to obtain a uniform composition. The composition so obtained was spread in a thickness of about 1 mm on a non-woven cloth as the support by the use of a spreader. The composition so supported was cooled to room temperature, covered with a polyethylene film and cut into a desired size to obtain plaster samples. When the plaster samples were tested for their efficacy by the application thereof to human bodies, they were found that they gave irritation to the skin of the human bodies due to the presence of the medicinal ingredient in the plaster and that they gave a feeling of close adhesion to the skin due to the flexibility and moderate adhesiveness of the plaster but they were easily releasable or removable, this proving that as a topicum, the plaster of this invention has both of said advantageous properties (satisfactory adhesion and releasability which are conflicting with each other) which it has been difficult for conventional plasters to possess.

EXAMPLE 2

One hundred (100) parts of a styrene-isoprene-styrene radial TR block copolymer (produced under the trademark of Solprene 418 by Phillips Petroleum Co.), 150 parts of liquid paraffin (produced under the trademark of Crystol 335 by Esso Standard Oil Co.), 40 parts of a rosin-modified maleic resin (Malkyd 2-N as defined before) and 10 parts of a hydrogenated rosin ester (produced under the trademark of Eastergum H by Arakawa Chemical Co.), were melted in a nitrogen gas stream. The resulting melt (about 150° C.) was cooled to about 120° C., incorporated with 30 parts of methyl salicylate and 21 parts of l-menthol and then mixed together to obtain a uniform composition. The thus obtained composition was spread in a thickness of about $200\mu$ on a raised cloth by the use of a spreader, covered with a polypropylene film and cut into a desired size to obtain plaster samples. When the thus obtained plaster samples were applied to the human bodies, they were found to have approximately the same advantageous properties as those obtained in Example 1.

EXAMPLE 3

Seventy-five (75) parts of a styrene-isoprene-styrene TR block copolymer (as defined in Example 1), 25 parts of a styrene-butadiene-styrene TR block copolymer (Cariflex TR 1101, Shell Chemical Co., Ltd.), 250 parts of liquid paraffin (as defined in Example 1), 75 parts of a rosin-modified maleic resin (as defined in Example 1) and 25 parts of a hydrogenated rosin ester (as defined in Example 2), were melted in a nitrogen gas stream. The resulting melt (about 150° C.) was cooled to about 120° C., incorporated with 0.45 parts of capsaicin and 13.5 parts of glycol salicylate and then mixed together thereby to obtain a uniform composition. The thus obtained composition was spread in a thickness of about 1 mm on a non-woven cloth by the use of a spreader, covered with a Cellophane film and then cut into a desired size to obtain plaster samples. When the thus obtained plaster samples were applied to human bodies, they exhibited the same performances as those obtained in Example 1.

EXAMPLE 4

One hundred (100) parts of the same styrene-isoprene-styrene TR block copolymer as used in Example 1, 210 parts of the same liquid paraffin as used in Example 1 and 100 parts of the same rosin-modified maleic resin as used in Example 1, were melted in a nitrogen gas stream. The resulting melt (about 150° C.) was cooled to about 120° C., incorporated with 16.4 parts of glycol salicylate and 4.1 parts of capsicum extract and then mixed together thereby to obtain a uniform composition. The thus obtained composition was spread in a thickness of about 150 $\mu$ on a non-raised cloth by the use of a spreader, covered with a polyethylene film and then cut into a desired size to obtain plaster samples. When applied to human bodies, they exhibited the same performances as those obtained in Example 1.

EXAMPLE 5

One hundred (100) parts of the same styrene-isoprene-styrene radial TR block copolymer as used in Example 2, 250 parts of the same liquid paraffin as used in Example 1, 90 parts of the same rosin-modified maleic resin as used in Example 1 and 10 parts of the same hydrogenated rosin ester as used in Example 2, were melted in a nitrogen gas stream. The resulting melt (about 150° C.) was cooled to about 120° C., incorporated with 22.5 parts of Voltaren (diclofenac sodium) and mixed together thereby to obtain a uniform composition. The composition so obtained was spread in a thickness of about $300\mu$ on a raised cloth by the use of a spreader, covered with a polypropylene film and then cut into a desired size to obtain plaster samples. When applied to human bodies, the plaster samples exhibited the same advantages as those obtained in Example 1.

EXAMPLE 6

Ninety (90) parts of the same styrene-isoprenestyrene radial TR block copolymer as used in Example 2, 10 parts of a styrene-butadiene-styrene radial TR block copolymer (produced under the trademark of Solprene T-414 by Nippon Elastomer Co., Ltd.), 300 parts of liquid paraffin (produced under the trademark of Crystol 70 by Esso Standard Oil Company) and 150 parts of the same rosin-modified maleic resin as used in Example 1, were melted in a nitrogen gas stream. The resulting melt (about 150° C.) was cooled to about 120° C., incorporated with 16.5 parts of glycol salicylate, 16.5 parts of l-menthol and 5 parts of dl-camphor and mixed together thereby to obtain a uniform composition. The composition so obtained was spread in a thickness of about 200μ on a raised cloth by the use of a spreader, covered with a Cellophane film and cut into a desired size thereby to obtain plaster samples. When applied to human bodies, the thus obtained plaster samples exhibited the same performances as those obtained in Example 1.

EXAMPLE 7

One hundred (100) parts of the same styrene-isoprene-styrene TR block copolymer as used in Example 1, 193 parts of the same liquid paraffin as used in Example 1 and 125 parts of the same hydrogenated rosin ester as used in Example 2, were melted in a nitrogen gas stream. The resulting melt (about 150° C.) was cooled to about 120° C., incorporated with 22 parts of 2-(p-isobutylphenyl) propionic acid-2-pyridyl methyl ester and then mixed together thereby to obtain a uniform composition. The composition so obtained was spread in a thickness of about 50μ on a non-raised cloth by the use of a spreader, covered with a polyethylene film and then cut into a desired size thereby to obtain plaster samples. When applied to human bodies, the thus obtained plaster samples gave a feeling of their close adhesion to the skin while they exhibited satisfactory releasability therefrom, these satisfactory adhesiveness and releasability being advantageous to the plaster.

EXAMPLE 8

One hundred (100) parts of the same styrene-isoprene-styrene radial TR block copolymer as used in Example 2, 80 parts of the same hydrogenated rosin ester as used in Example 2, 135 parts of the same liquid paraffin as used in Example 2 and 20 parts of the same rosin-modified maleic resin as used in Example 1, were melted in a nitrogen gas stream. The resulting melt (about 150° C.) was cooled to about 120° C., incorporated with 17.6 parts of ethyl ester of ketoprofen and mixed together thereby to obtain a uniform composition. The composition so obtained was spread in a thickness of about 50μ on a non-woven cloth by the use of a spreader, covered with a polypropylene film and cut into a desired size thereby to obtain plaster samples. When applied to human bodies, the thus obtained plaster samples exhibited the same performances as those obtained in Example 7.

EXAMPLE 9

Seventy-five (75) parts of the same styrene-isoprene-styrene TR block copolymer as used in Example 1, 25 parts of a styrene-butadiene-styrene TR block copolymer (produced under the trademark of Cariflex TR 1102 by Shell Chemical Co., Ltd.), 145 parts of the same liquid paraffin as used in Example 1, 100 parts of the same rosin ester as used in Example 2 and 50 parts of the same rosin-modified maleic resin as used in Example 1, were melted in a nitrogen gas stream. The resulting melt (about 150° C.) was cooled to about 120° C., incorporated with 20.8 parts of clidanac and mixed together thereby to obtain a uniform composition. The composition so obtained was spread in a thickness of about 30μ on a 25μ thick polyester film by the use of a spreader-covered with releasable paper (this meaning "paper, treated so that it may be easily releasable" throughout the specification and claims) and cut into a desired size thereby to obtain plaster samples. When applied to human bodies, the thus obtained plaster samples exhibited the same performances as those obtained in Example 7.

EXAMPLE 10

One hundred (100) parts of the same styrene-isoprene-styrene TR block copolymer as used in Example 1, 185 parts of liquid paraffin (produced under the trademark of Moresco-White P-350 by Nippon Oil Co., Ltd.) and 50 parts of the same hydrogenated rosin ester as used in Example 2, were melted in a nitrogen gas stream. The resulting melt (about 150° C.) was cooled to about 120° C., incorporated with 10.4 parts of ketoprofen and mixed together thereby to obtain a uniform composition. The composition so obtained was spread in a thickness of about 50μ on a non-woven cloth by the use of a spreader, covered with a polypropylene film and cut into a desired size thereby to obtain plaster samples. When applied to human bodies, the thus obtained plaster samples exhibited the same performances as those obtained in Example 7.

EXAMPLE 11

Ninety (90) parts of the same styrene-isoprene-styrene radial TR block copolymer as used in Example 2, 10 parts of a styrene-butadiene-styrene radial TR block copolymer (produced under the trademark of Solprene T-431 by Asahi Kasei Co., Ltd.), 310 parts of the same liquid paraffin as used in Example 6, 110 parts of the same hydrogenated rosin ester as used in Example 2 and 65 parts of the same rosin-modified maleic resin as used in Example 1, were melted in a nitrogen gas stream. The resulting melt (about 150° C.) was cooled to about 120° C., incorporated with 5.9 parts of alclofenac and mixed together thereby to obtain a uniform composition. The composition so obtained was spread in a thickness of about 90μ on a raised cloth by the use of a spreader, covered with a polyethylene film and cut into a desired size thereby to obtain plaster samples. When applied to human bodies, the thus obtained plaster samples exhibited the same performances as those obtained in Example 7.

EXAMPLE 12

Sixty (60) parts of the same styrene-isoprene-styrene TR block copolymer as used in Example 1, 40 parts of the same styrene-isoprene-styrene radial TR block copolymer as used in Example 2, 300 parts of the same liquid paraffin as used in Example 2, 60 parts of the same hydrogenated rosin ester as used in Example 2 and 15 parts of the same rosin-modified maleic resin as used in Example 1, were melted in a nitrogen gas stream. The resulting melt (about 150° C.) was cooled to about 120° C., incorporated with 25 parts of indomethacin and mixed together thereby to obtain a uniform composition. The composition so obtained was spread in a thickness of about 50μ on a non-woven cloth by the use of a spreader, covered with a releasable paper and cut into a desired size thereby to obtain plaster samples. When applied to human bodies, the thus obtained plaster samples exhibited the same performances as those obtained in Example 7.

EXAMPLE 13

One hundred (100) parts of the same styrene-isoprene-styrene TR block copolymer as used in Example 1,250 parts of the same liquid paraffin as used in Example 2, 60 parts of the same hydrogenated rosin ester as used in Example 2 and 90 parts of the same rosin-modified maleic resin as used in Example 1, were melted in a nitrogen gas stream. The resulting melt (about 150° C.) was cooled to about 120° C., incorporated with 5.1 parts of flurbiprofen and mixed together thereby to obtain a uniform composition. The composition so obtained was spread in a thickness of about 90μ on a staple fiber cloth by the use of a spreader, covered with a polypropylene film and cut into a desired size thereby to obtain plaster samples. When applied to human bodies, the thus obtained plaster samples exhibited the same performances as those obtained in Example 7.

EXAMPLE 14

One hundred (100) parts of the same styrene-isoprene-styrene TR block copolymer as used in Example 1, 150 parts of the same liquid paraffin as used in Example 2 and 150 parts of the same hydrogenated rosin ester as used in Example 2, were melted in a nitrogen gas stream. The resulting melt (about 150° C.) was cooled to about 120° C., incorporated with 21.05 parts of etofenamate and mixed together thereby to obtain a uniform composition. The composition so obtained was spread in a thickness of 90μ on a releasable paper by the use of a spreader and cooled, after which a 60μ thick polyethylene film was pressed on the composition-spread releasable paper to transfer the composition layer therefrom to the polyethylene film. The resulting polyethylene film-supported composition layer was cut into a desired size to obtain plaster samples. When applied to human bodies, the thus obtained plaster samples exhibited the same performances as those obtained in Example 7.

EXAMPLE 15

Sixty (60) parts of the same styrene-isoprene-styrene TR block copolymer as used in Example 1, 40 parts of a styrene-isoprene-styrene radial TR block copolymer as used in Example 2, 300 parts of the same liquid paraffin as used in Example 2, 60 parts of the same hydrogenated rosin ester as used in Example 2 and 15 parts of the rosin-modified maleic resin as used in Example 1, were melted in a nitrogen gas stream. The resulting melt (about 150° C.) was cooled to about 120° C., incorporated with 25 parts of carboxymethyl ester of indomethacin and mixed together thereby to obtain a uniform composition. The composition so obtained was spread in a thickness of 50μ on a releasable paper by the use of a spreader and cooled, after which a 60μ thick polyethylene film was pressed on the composition-spread releasable paper to transfer the composition layer to the polyethylene film. The composition layer supported by the polyethylene film was cut into a desired size to obtain plaster samples. When applied to human bodies, the thus obtained plaster samples exhibited the same performances as those obtained in Example 7.

EXAMPLE 16

Ninety (90) parts of the same styrene-isoprene-styrene radial TR block copolymer as used in Example 2, 10 parts of the same styrene-butadiene-styrene radial TR block copolymer as used in Example 11, 308.99 parts of the same liquid paraffin as used in Example 6, 110 parts of the same hydrogenated rosin ester as used in Example 2 and 65 parts of the rosin-modified maleic resin as used in Example 1, were melted in a nitrogen gas stream. The resulting melt (about 150° C.) was cooled to about 120° C., incorporated with 5.90 parts of n-butyl ester of fulfenamic acid and mixed together thereby to obtain a uniform composition. The composition so obtained was spread in a thickness of about 90μ on a releasable paper by the use of a spreader and cooled, after which a 80μ thick soft polyvinyl chloride film was pressed to the composition-spread releasable paper to transfer the composition layer therefrom to the film. The film-supported composition layer was cut into a desired size thereby to obtain plaster samples. When applied to human bodies, the thus obtained plaster samples exhibited the same performances as those obtained in Example 7.

EXAMPLE 17

One hundred (100) parts of the same styrene-isoprene-styrene TR block copolymer as used in Example 1, 150 parts of the same liquid paraffin as used in Example 1, 90 parts of the same hydrogenated rosin ester as used in Example 2 and 60 parts of the same rosin-modified maleic resin as used in Example 1, were melted in a nitrogen gas stream. The resulting melt (about 150° C.) was cooled to about 120° C., incorporated with 25 parts of glycol salicylate (produced under the trademark of Salocoll by Yoshitomi Pharmaceutical Co., Ltd.) and 25 parts of l-menthol and mixed together thereby to obtain a uniform composition. The composition so obtained was spread in a thickness of about 90μ on a releasable paper by the use of a spreader and cooled, after which an about 60μ thick polyethylene film was pressed on the composition-spread releasable paper to transfer the composition layer therefrom to the film. The film-supported composition layer was cut into a desired size thereby to obtain plaster samples. When applied to human bodies, the thus obtained plaster samples exhibited the same performances as those obtained in Example 1.

EXAMPLE 18

One hundred (100) parts of the same styrene-isoprene-styrene radial TR block copolymer as used in Example 2, 100 parts of the same liquid paraffin as used in Example 2 and 100 parts of the same hydrogenated rosin ester as used in Example 2, were melted in a nitrogen gas stream. The resulting melt (about 150° C.) was cooled to about 120° C., incorporated with 20 parts of glycol salicylate and 20 parts of l-menthol and mixed together thereby to obtain a uniform composition. The composition so obtained was spread in a thickness of about 90μ on a non-woven cloth by the use of a spreader, covered with a releasable paper and cut into a desired size thereby to obtain plaster samples. When applied to human bodies as in Example 17, the thus obtained plaster samples exhibits the same performances as those obtained in Example 17.

EXAMPLE 19

Seventy-five (75) parts of the same styrene-isoprene-styrene TR block copolymer as used in Example 1, 25 parts of the same styrene-butadiene-styrene TR block copolymer as used in Example 9, 200 parts of the same liquid paraffin as used in Example 1, 50 parts of the same rosin-modified maleic resin as used in Example 1 and 75 parts of the same hydrogenated rosin ester as used in Example 2, were melted in a nitrogen gas stream. The resulting melt (about 150° C.) was cooled to about 120° C., incorporated with 27 parts of glycol salicylate and 27 parts of l-methanol and mixed together thereby to obtained a uniform composition. The composition so obtained was spread in a thickness of about 90μ on a releasable paper by the use of a spreader and cooled, after which an about 120μ thick soft polyvinyl chloride sheet was pressed on the composition-spread paper to transfer the composition layer therefrom to the polymer sheet and was cut into a desired size thereby to obtain plaster samples. When applied to human bodies, the thus obtained plaster samples exhibited the same performances as those obtained in Example 17.

EXAMPLE 20

Ninety (90) parts of the same styrene-isoprene-styrene radial TR block copolymer as used in Example 2, 10 parts of the same styrene-butadiene-styrene radial TR block copolymer as used in Example 11, 250 parts of the same liquid paraffin as used in Example 10 and 175 parts of the same rosin-modified maleic resin as used in Example 1, were melted in a nitrogen gas stream. The resulting melt (about 150° C.) was cooled to about 120° C., incorporated with 33 parts of glycol salicylate and 33 parts of l-menthol and mixed together thereby to obtain a uniform composition. The composition so obtained was spread by the use of a spreader as in Example 17 thereby to obtain plaster samples. When applied to human bodies, the thus obtained plaster samples exhibited the same performances as those obtained in Example 17.

EXAMPLE 21

Eighty (80) parts of the same styrene-isoprene-styrene radial TR block copolymer as used in Example 2, 20 parts of the same styrene-butadiene-styrene TR block copolymer as used in Example 9, 250 parts of the same liquid paraffin as used in Example 6 and 100 parts of the same hydrogenated rosin ester as used in Example 2, were melted in a nitrogen gas stream. The resulting melt (about 150° C.) was cooled to about 120° C., incorporated with 28 parts of glycol salicylate and 28 parts of l-menthol and mixed together thereby to obtain a uniform composition. The composition so obtained was spread by the use of a spreader as in Example 17 thereby to obtain plaster samples. When applied to human bodies, the thus obtained plaster samples exhibited the same performances as those obtained in Example 17.

EXAMPLE 22

One hundred (100) parts of the same styrene-isoprene-styrene TR block copolymer as used in Example 1, 150 parts of the same liquid paraffin as used in Example 2 and 75 parts of the same hydrogenated rosin ester as used in Example 2, were melted in a nitrogen gas stream. The resulting melt (about 150° C.) was cooled to about 120° C., incorporated with 6 parts of methyl salicylate, 15 parts of glycol salicylate and 20 parts of l-menthol and mixed together thereby to obtain a uniform composition. The composition so obtained was spread by the use of a spreader as in Example 17 thereby to obtain plaster samples. When applied to human bodies, the thus obtained plaster samples exhibited the same performances as those obtained in Example 17.

EXAMPLE 23

One hundred (100) parts of the same styrene-isoprene-styrene TR block copolymer as used in Example 1, 100 parts of the same liquid paraffin as used in Example 2 and 50 parts of the same hydrogenated rosin ester as used in Example 2, were melted in a nitrogen gas stream. The resulting melt (about 150° C.) was cooled to about 120° C., incorporated with 10 parts of peppermint oil, 6 parts of glycol salicylate, 10 parts of l-menthol, 5 parts of dl-camphor and 1 part of thymol and then mixed together thereby to obtain a uniform composition. The composition so obtained was spread in a thickness of about 90μ on a 25μ thick polyester film by the use of a spreader, covered with a releasable paper and cut into a desired size thereby to obtain plaster samples. When applied to human bodies, the thus obtained plaster samples exhibited the same performances as those obtained in Example 17.

EXAMPLE 24

One hundred (100) parts of the same styrene-isoprene-styrene TR block copolymer as used in Example 1, 182 parts of the same liquid paraffin as used in Example 1 and 125 parts of the same hydrogenated rosin ester as used in Example 2, were melted at 130° C. –170° C. in a nitrogen gas stream. The resulting melt was cooled to lower than 150° C., incorporated with a solution of 0.3336 parts of flurandolenoride in 10 parts of sorbitan trioleate (trademark, SO-30; Nikko Chemicals Co., Ltd.) and then mixed together thereby to obtain a uniform composition. The composition so obtained was spread in a thickness of about 50μ on a releasable paper by the use of a spreader and cooled, after which a 60μ thick polyethylene film was pressed onto the composition-spread paper to transport the composition layer thereform to the film and was cut into a desired size thereby to obtain plaster samples. When applied to human bodies, the thus obtained plaster samples exhibited the same performances as those obtained in Example 1.

EXAMPLE 25

One hundred (100) parts of the same styrene- isoprene-styrene radial TR block copolymer as used in Example 2, 123.4 parts of the same liquid paraffin as used in Example 2, 80 parts of the same hydrogenated rosin ester as used in Example 2 and 20 parts of the same rosin-modified maleic resin as used in Example 1, were melted in a nitrogen gas stream. The resulting melt was cooled to lower than about 150° C., incorporated with a solution of 0.2669 parts of fludroxycortido in 10 parts of sorbitan sesquioleate (trademark, SO-15; Nikko Chemical Co., Ltd.) and then mixed together thereby to obtain a uniform composition. The composition so obtained was spread as in Example 24 thereby to obtain plaster samples. When applied to human bodies, the thus obtained plaster sample exhibited the same performances as those obtained in Example 24.

EXAMPLE 26

Seventy-five (75) parts of the same styrene-isoprene-styrene TR block compolymer as used in Example 1, 25 parts of a styrene-butadiene-styrene TR block copolymer as used in Example 9, 128 parts of the same liquid paraffin as used in Example 1, 100 parts of the same hydrogenated rosin ester as used in Example 2 and 50 parts of the same rosin-modified maleic resin as used in Example 1, were melted in a nitrogen gas stream. The resulting melt was cooled to lower than about 150° C., incorporated with a solution of 0.6228 parts of fluocinolone acetonide in 10 parts of sorbitan monostearate (SO-10, Nikko Chemicals Co., Ltd.) and then mixed together thereby to obtain a uniform composition. The composition so obtained was spread in a thickness of 50μ on a releasable paper by the use of a spreader and cooled, after which a non-woven cloth was pressed onto the composition-spread paper to transfer the composition layer therefrom to the cloth and cut into a desired size thereby to obtain plaster samples. When applied to human bodies, the thus obtained plaster samples exhibited the same performances as those obtained in Example 24.

EXAMPLE 27

One hundred (100) parts of the same styrene-isoprene-styrene TR block copolymer as used in Example 1, 172 parts of the same liquid paraffin as used in Example 10 and 50 parts of the same hydrogenated rosin ester as used in Example 2, were melted in a nitrogen gas stream. The resulting melt was cooled to about 150° C., incorporated with a solution of 2 parts of prednisolone in 10 parts of tripolyoxyethylene alkyl ether phosphase (TOP-2, Nikko Chemical Co., Ltd.) and then mixed together thereby to obtain a uniform comosition. the composition so obtained was spread in a thickness of 50μ on a releasable paper by the use of a spreader and cooled, after which an about 120μ thick polyvinyl chloride sheet was pressed onto the composition-spread paper to transfer the composition layer therefrom to the polymer sheet and was cut into a desired size thereby to obtain plaster samples. When applied to human bodies, the thus obtained plaster samples exhibited the same performances as those obtained in Example 24.

EXAMPLE 28

Ninety (90) parts of the same styrene-isoprene-styrene radial TR block copolymer as used in Example 2, 10 parts of a styrene-butadiene-styrene radial TR block copolymer as used in Example 11, 298.4 parts of the same liquid paraffin as used in Example 6, 105 parts of the same hydrogenated rosin ester as used in Example 2 and 65 parts of the same rosin-modified maleic resin as used in Example 1, were melted in a nitrogen gas stream. The resulting melt was cooled to lower than about 150° C., incorporated with a solution of 0.4671 parts of flurandolenoride in 10 parts of dipolyoxyethylene alkyl ether phosphate (DOP-2, Nikko Chemicals Co., Ltd.) and then mixed together thereby to obtain a uniform composition. The composition so obtained was spread in a thickness of about 50μ on a 25μ thick polyester film by the use of a spreader, covered with a releasable paper and cut into a desired size thereby to obtain plaster samples. When applied to human bodies, the thus obtained plaster samples exhibited the same performances as those obtained in Example 24.

EXAMPLE 29

Sixty (60) parts of the same styrene-isoprene-styrene TR block copolymer as used in Example 1, 40 parts of a styrene-isoprene-styrene radial TR block copolymer as used in Example 2, 287.3 parts of the same liquid paraffin as used in Example 2, 60 parts of the same hydrogenated rosin ester as used in Example 2 and 15 parts of the same rosin-modified maleic resin as used in Example 1, were melted in a nitrogen gas stream. The resulting melt was cooled to lower than about 150° C., incorporated with a solution of 0.3781 parts of fludroxycortido in 10 parts of sorbitan trioleate (SO-30, Nikko Chemicals Co., Ltd.) and then mixed together thereby to obtain a uniform composition. The composition so obtained was spread as in Example 24 and cut into a desired size thereby to obtain plaster samples. When applied to human bodies, the thus obtained plaster samples exhibited the same performances as those obtained in Example 24.

EXAMPLE 30

One hundred (100) parts of the same styrene-isoprene-styrene TR block copolymer as used in Example 1, 240 parts of the same liquid paraffin as used in Example 2, 60 parts of the same hydrogenated rosin ester as used in Example 2 and 90 parts of the same rosin modified maleic resin as used in Example 1, were melted in a nitrogen gas stream. The resulting melt was cooled to lower than about 150° C., incorporated with a solution of 0.4004 parts of flurandolenoride in 10 parts of sorbitan monooleate (SO-10, Nikko Chemicals Co., Ltd.) and then mixed together thereby to obtain a uniform composition. The composition so obtained was spread in a thickness of about 50μ on a non-woven cloth by the use of a spreader, covered with a releasable paper and cut into a desired size thereby to obtain plaster samples. When applied to human bodies, the thus obtained plaster samples exhibited the same performances as those obtained in Example 24.

EXAMPLE 31

One hundred (100) parts of the same styrene-isoprene-styrene TR block copolymer as used in Example 1, 195 parts of the same liquid paraffin as used in Example 2 and 125 parts of the same hydrogenated rosin ester as used in Example 2, were melted in a nitrogen gas stream. The resulting melt (about 150° C.) was cooled to about 120° C., incorporated with 17.5 parts of indoprofen and then mixed together thereby to obtain a uniform composition. The composition so obtained was spread in a thickness of 50μ on a releasable paper by the use of a spreader and cooled, after which a 60μ thick polyethylene film was pressed onto the composition-spread paper to transfer the composition layer therefrom to the polymer film and was cut into a desired size thereby to obtain plaster samples. When applied to human bodies, the thus obtained plaster samples exhibited the same performances as those obtained in Example 7.

EXAMPLE 32

One hundred (100) parts of the same styrene-isoprene-styrene TR block copolymer as used in Example 1, 193 parts of the same liquid paraffin as used in Example 1 and 125 parts of the same hydrogenated rosin ester as used in Example 2, were melted in a nitrogen gas stream. The resulting melt (about 150° C.) was cooled to about 120° C., incorporated with 12.93 parts of hydroxyethylester of Ketoprofen and then mixed together therebyto obtain a uniform composition. The composition so obtained was spread in a thickness of about 90μ on a non-raised cloth by the use of a spreaded, covered with a polyethylene film and then cut into a desired size thereby to obtain plaster samples. When applied to human bodies, the thus obtained plaster samples gave a feeling of their close adhesion to the skin while they exhibited satisfactory releasability therefrom, these satisfactory adhesiveness and releasability being advantageous to the plaster.

EXAMPLE 33

One hundred (100) parts of the same styrene-isoprene-styrene TR block copolymer as used in Example 1, 193 parts of the same liquid paraffin as used in Example 1 and 125 parts of the same hydrogenated rosin ester as used in Example 2, were melted in a nitrogen gas stream. The resulting melt (about 150° C.) was cooled to about 120° C., incorporated with 12.93 parts of Oxepinac and then mixed together thereby to obtain a uniform composition. The composition so obtained was spread in a thickness of about 90μ on a non-raised cloth by the use of a spreader, covered with a polyethylene film and then cut into a desired size thereby to obtain plaster samples. When applied to human bodies, the thus obtained plaster samples gave a feeling of their close adhesion to the skin while they exhibited satisfactory releasability therefrom, these satisfactory adhesiveness and releasability being advantageous to the plaster.

EXAMPLE 34

One hundred (100) parts of the same styrene-isoprene-styrene TR block copolymer as used in Example 1, 193 parts of the same liquid paraffin as used in Example 1 and 125 parts of the same hydrogenated rosin ester as used in Example 2, were melted in a nitrogen gas stream. The resulting melt (about 150° C.) was cooled to about 120° C., incorporated with 12.93 parts of pranoprofen and then mixed together thereby to obtain a uniform composition. The composition so obtained was spread in a thickness of about 90μ on a non-raised cloth by the use of a spreader, covered with a polyethylene film and then cut into a desired size thereby to obtain plaster samples. When applied to human bodies, the thus obtained plaster samples gave a feeling of their close adhesion to the skin while they exhibited satisfactory releasability therefrom, these satisfactory adhesiveness and releasability being advantageous to the plaster.

EXAMPLE 35

One hundred (100) parts of the same styrene-isoprene-styrene TR block copolymer as used in Example 1, 193 parts of the same liquid paraffin as used in Example 1 and 125 parts of the same hydrogenated rosin ester as used in Example 2, were melted in a nitrogen gas stream. The resulting melt (about 150° C.) was cooled to about 120° C., incorporated with 12.93 parts of Benoxaprofen and then mixed together thereby to obtain a uniform composition. The composition so obtained was spread in a thickness of about 90μ on a non-raised cloth by the use of a spreader, covered with a polyethylene film and then cut into a desired size thereby to obtain plaster samples. When applied to human bodies, the thus obtained plaster samples gave a feeling of their close adhesion to the skin while they exhibited satisfactory releasability therefrom, these satisfactory adhesiveness and releasability being advantageous to the plaster.

EXAMPLE 36

One hundred (100) parts of the same styrene-isoprene-styrene TR block copolymer as used in Example 1, 193 parts of the same liquid paraffin as used in Example 1 and 125 parts of the same hydrogenated rosin ester as used in Example 2, were melted in a nitrogen gas stream. The resulting melt (about 150° C.) was cooled to about 120° C., incorporated with 12.93 parts of piroxican and then mixed together thereby to obtain a uniform composition. The composition so obtained was spread in a thickness of about 90μ on a non-raised cloth by the use of a spreader, covered with a polyethylene film and then cut into a desired size thereby to obtain plaster samples. When applied to human bodies, the thus obtained plaster samples gave a feeling of their close adhesion to the skin while they exhibited satisfactory releasability therefrom, these satisfactory adhesiveness and releasability being advantageous to the plaster.

EXAMPLE 37

One hundred (100) parts of the same styrene-isoprene-styrene TR block copolymer as used in Example 1, 193 parts of the same liquid paraffin as used in Example 1 and 125 parts of the same hydrogenated rosin ester as used in Example 2, were melted in a nitrogen gas stream. The resulting melt (about 150° C.) was cooled to about 120° C., incorporated with 12.93 parts of Fentiazac and then mixed together thereby to obtain a uniform composition. The composition so obtained was spread in a thickness of about 90μ on a non-raised cloth by the use of a preader, covered with a polyethylene film and then cut into a desired size thereby to obtain plaster samples. When applied to human bodies, the thus obtained plaster samples gave a feeling of their close adhesion to the skin while they exhibited satisfactory releasability therefrom, these satisfactory adhesiveness and releasability being advantageous to the plaster.

Experiments will be made to explain the pharmacological action of the plaster of this invention.

EXPERIMENT 1

Comparison of topical anti-infammatory activity on carrageenin-induced dorsal cutaneous edema in rats Male rats (6 or 7 of the rats forming one group) of Wistar strain, weighing 95-105 g, were depilated with Eba Cream (tradename, a depilatory produced by Tokyo Tanabe Pharmaceutical Co., Ltd.). Twenty-four (24) hours after the depilation, 0.1 ml of a physiological salt solution containing 1% of carrageenin (Picnin A produced by Pasco International Co.) was injected into one side of the dorsal skin of the rats, and only a physiological solution (containing no carrageenin) was injected into the other side thereof, these sides being positioned symmetrically to each other with respect to the backbone of the rats. Immediately after the injection, the plaster (1.5 cm×1.5 cm) of Example 14 and a vinyl resin sheet (1.5 cm×1.5 cm) coated with the following gel containing the same medicinal ingredient of the plaster of Example 14 in the same proportion as in said plaster, were applied respectively to the injected sites of the dorsal skin. Two and a half hours later, 0.5 ml/100 g (body weight) of a 1% solution of pontamine sky blue 6B (a dye produced by Yoneyama Pharmaceutical Co., Ltd.) was intravenously injected to the rats, and 30 minutes after this intravenous injection, the rats so injected were allowed to die by bloodletting. The skin of the dead rats was peeled therefrom and then measured for thickness at the carrageenin injected site with a dial thickness gauge (pressure 40 g, manufactured by Peacock Co.). The swelling (%) at the edema portion of the skin was calculated as follows.

$$\text{Swelling (\%)} = \frac{\text{Thickness of skin at carrageenin injected site} - \text{Thickness of skin at physiological salt solution injected site}}{\text{Thickness of skin at physiological salt solution injected site}} \times 5$$

Further, the dye extravasating area (cm²) was calculated by multiplying the long diameter by the short diameter in the dye extravasating portion of the skin. Still further, the pontamine sky blue 6B present at this skin portion was extracted to find the amount (μg) of the extravasating dye by the use of the Harada et al method (J. Pharmaceut. Pharmacol., 23, 218, 1971 M. Harada et al).

In each run of the experiment, the treated groups were compared with the non-treated (non-use of the plaster and gel) group by the use of "t-inspection (or t-test)".

The said gel used as the control had the following composition.

| | |
|---|---|
| Etofenamate | 5 Parts by weight |
| Propylene glycol | 27 Parts by weight |
| Purified water | 25.42 Parts by weight |
| Isopropyl alcohol | 40 Parts by weight |
| Carboxyvinyl polymer | 1 Parts by weight |
| Hydroxypropylcellulose | 1.5 Parts by weight |
| Triethanolamine | 0.08 Parts by weight |

TABLE 1

Antiinflammatory effects of 5% Etofenamate plaster and 5% Etofenamate gel on carrageenin-induced dorsally cutaneous edema in rats

| | wt. of base | no. of rats | % of swelling | area [cm²] of dye | amount [μg] of dye |
|---|---|---|---|---|---|
| Non-treated | — | 7 | 85.5 ± 4.0 | 0.79 ± 0.13 | 27.3 ± 4.3 |
| Plaster-control | 20 mg | 7 | 71.33 ± 3.6* [16.6] | 0.60 ± 0.06 [24.1] | 19.3 ± 1.4 [29.3] |
| 5% Etofenamate plaster (Ex. 14) | 20 mg | 7 | 45.3 ± 3.3**°° [47.0](36.4) | 0.21 ± 0.05**°° [73.4](65.0) | 13.5 ± 1.0*°° [50.5](29.9) |
| Gel-control | 20 mg | 7 | 73.2 ± 6.0 [14.3] | 0.69 ± 0.07 [12.7] | 23.2 ± 3.4 [14.8] |
| 5% Etofenamate gel | 20 mg | 6 | 47.6 ± 4.3**°° [44.3](35.0) | 0.20 ± 0.07**°° [74.7](71.0) | 14.9 ± 1.8* [45.5](36.1) |

Significant difference from non-treated, respectively: *p < 0.05, **p < 0.01
Significant difference from each control, respectively: °p < 0.05, °°p < 0.01
Significant difference between plaster- and gel-control, or between MG-585 plaster and MG585 gel, respectively: ˙p < 0.05, ˙˙p < 0.01
[ ]: inhibitory % from non-treated
( ): inhibitory % from each control As is apparent from the results shown in Table 1, the plaster of this invention exhibited the same effects as the gel and also exhibited a significant inhibiting action under the same conditions as in the gel.

EXPERIMENT 2

Comparison of effects on carrageenin-induced cutaneous edema in rats

The procedure of Experiment 1 was followed except that the base material of Example 7 and the plaster thereof were substituted for the plaster of Example 14 and the gel, respectively. In each of the experiments, the non-treated group and the plaster-treated group were each compared with the base material-treated group by the use of "t-inspection (t-test)".

The test results are as shown in Tables 2 to 4.

TABLE 2

(Comparison of the plaster of Example 7 with the base material thereof)

| | No. of rats tested | Swelling (%) | Dye extravasating area (cm²) | Amount of dye extravasated (μg) |
|---|---|---|---|---|
| Non-treated group | 8 | 74.7 ± 3.5 | 0.78 ± 0.07 | 20.2 ± 1.0 |
| Base material (Ex. 7)-treated group | 8 | 61.3 ± 3.2 | 0.70 ± 0.04 | 19.4 ± 1.1 |
| Plaster (Ex. 7)-treated group | 7 | 35.9 ± 2.1** (41.5) | 0.16 ± 0.05** (77.1) | 11.9 ± 0.9** (38.5) |

( ): Inhibition ratio to the base material-treated group.
**: P < 0.01, this indicating there is a significant difference.

In each run of the above experiment, the plaster and base material used were each 1.5 cm × 1.5 cm (square) in size.

As is apparent from the results shown in Table 2, the plaster of this invention exhibited a significant (P<0.01) inhibiting action on the swelling, dye extravasating area and amount of dye extravasated. In addition, the said results suggest that the medicinal ingredinet was discharged from the base material in the plaster.

TABLE 3

(Comparison of the plaster of Example 17 with a commercially available similar medicine "SECOURS (tradename)" produced by Yutoku Pharmaceutical Co., Ltd.)

| | Test item | | | |
|---|---|---|---|---|
| | No. of rats tested | Swelling (%) | Dye extravasalting area (cm²) | Amount of Dye extravasated (μg) |
| Non-treated group | 12 | 75.8 ± 2.6 | 0.59 ± 0.02 | 17.1 ± 0.6 |
| Plaster (Ex. 17)-treated group | 12 | 49.8 ± 1.3** (34.3) | 0.18 ± 0.01** (69.5) | 9.2 ± 0.1** (46.1) |
| SECOURS-treated group | 12 | 50.5 ± 1.5** (33.3) | 0.18 ± 0.01** (69.5) | 9.1 ± 1.2** (46.6) |

( ): Inhibition ratio to the non-treated group.
**: P < 0.01, this indicating there is a significant difference.

The plaster and SECOURS samples used were each 1.5 cm × 1.5 cm (square) in size.

As is clear from the results shown in Table 3, the plaster of this invention exhibited the same effects as SECOURS. Thus, it exhibited a significant inhibiting action on any of the test items.

TABLE 4

(Comparison of the plaster of Example 24 with dolenisone tapes)

| | Test item | | | |
|---|---|---|---|---|
| | No. of rats tested | Swelling (%) | Dye extravasating area (cm²) | Amount of Dye extravasated (μg) |
| Non-treated group | 9 | 75.3 ± 6.2 | 0.66 ± 0.09 | 18.2 ± 2.0 |
| Plaster (Ex. 24)-treated group | 10 | 41.4 ± 2.4** (45.0) | 0.01 ± 0.00** (98.5) | 6.8 ± 0.4** (62.6) |
| Dolenisone-treated group | 10 | 40.5 ± 2.4** (46.2) | 0.01 ± 0.00 (98.5) | 6.6 ± 0.5** (63.7) |

( ): Inhibition ratio to the non-treated group.
**: $P < 0.01$, this indicating there is a significant difference.

The plaster and dolenisone used were each circular with a 1.6-cm diameter. The plaster and dolenisone tapes contained 8 μg of their respective medicinal ingredient.

As is apparent from the above results, the plaster of this invention exhibited the same effects as the dolenisone tapes and also exhibited a significant inhibiting action on any of the test items.

EXPERIMENT 3

Comparison of effects on ultra violet irradiation-induced dorsal cutaneous erythema in guinea pigs The method for carrying out this experiment is the one which has heretofore been used as a method for evaluating orally administered anti-inflammatory drugs. In accordance with this method, the efficacy of the plaster of this invention was compared with that of a conventional plaster as follows.

Male guinea pigs of Hartley strain (10 of the pigs forming one group), weighing 300-500 g each, were depilated with depilatory cream (which was supplied under the trademark of Eva Cream in this case), left overnight as they were and then used. the depilated dorsal skin of each of the guinea pigs was covered with a thick ultraviolet light-interrupting cloth with 3 round holes (each having a 5-mm diameter) therethrough and irradiated with ultraviolet light for 20 seconds at a distance of about 25 cm from an ultraviolet irradiation device (500 W×2 ultraviolet lamps), immediately after which the plaster (Example 17) of this invention and the conventional plaster were applied to the irradiated skin portions (where erythema were formed) through the holes. Two hours and 55 minutes after the irradiation, these plasters and the remaining material were removed from the irradiated skin protions. Three (3) hours and 24 hours after the irradiation, the degree of erythema appearing on each of the irradiated skin portions was evaluated at 0.5 scale to be given one of numbers 0 to 4 (0: no change found, 1: slight erythema, 2: moderate erythema with its extent being not clearly defined, 3: erythema with its extent being clearly defined, 4: erythema with swelling and its extent being clearly defined).

The efficacy of the present and conventional plasters was evaluated by a total of numbers given to the degree of erythema on the three irradiated portions of each guinea pig. Thus, the total number given to one guinea pig was limited to 12 at most.

The test results are as shown in Tables 5-6.

TABLE 5

(Comparison of medicinal efficacy between the present plaster and SECOURS)

| | No. of guinea pigs tested | Degree of erythema formed 3 hours after irradiation | Degree of erythema formed 24 hours after irradiation |
|---|---|---|---|
| Non-treated group | 10 | 9.55 ± 0.28 | 9.05 ± 0.19 |
| Plaster (Example 17)-treated group | 10 | 5.15 ± 0.20** (46.1) | 6.20 ± 0.28** (31.5) |
| SECOURS-treated group | 10 | 5.20 ± 0.20** (45.5) | 6.40 ± 0.21** (29.3) |

( ): Inhibition ratio to the non-treated group.
**: $P < 0.01$, this indicating there is a significant difference.

The plasters used were each 1.5 cm × 1.5 cm (square) in size.

As is apparent from the above results, the plaster of this invention exhibited the same efficacy as SECOURS and was found to have a significant inhibiting action on erythema formation.

TABLE 6

(Comparison of efficacy between the plaster of Example 24 and dolenisone tape)

| | No. of guinea pigs tested | Degree of erythema formed 3 hours after irradiation | Degree of erythema formed 24 hours after irradiation |
|---|---|---|---|
| Non-treated group | 7 | 9.36 ± 0.47 | 8.43 ± 0.43 |
| Plaster (Example 24)-treated group | 7 | 6.64 ± 0.57** (29.1) | 7.07 ± 0.37** (16.1) |
| Dolenisone-treated group | 7 | 6.71 ± 0.42** (28.3) | 6.86 ± 0.46** (18.6) |

( ): Inhibition ratio to the non-treated group.
**: $P < 0.01$, this indicating there is a significant difference.

The test samples used were each circular with a 1.6-cm diameter. The plaster (Example 24) and dolenisone tapes contained 8μg of their respective medicinal ingredient.

As is apparent from the above results, the plaster of this invention exhibited the same effect as the dolenisone tape.

EXPERIMENT 4

Experiment for the inhibiting action on rabbit anti-rat serum-induced cutaneous edema in rats Four-week-old male rats (11-12 rats forming a group) of Wistar strain, weighing approximately 100 g each, were depilated with Eba Cream (a depilatory as previously defined) and left overnight as they were. For 2.5 hours before the injection the plaster (containing 8μg of the medicinal ingredient and being circular with a 1.6-cm diameter) of Example 24 and a dolenisone tape (containing 8μg of dolenisone and being circular with a 1.6-cm diameter) were applied respectively to the sites of the dorsal skin to be injected. Thereafter, these plaster and tape were removed from said sites. Then, 0.1 ml of rabbit anti-rat serum was injected into one side of the dorsal skin of the rats, while 0.1 ml of a physiological salt solution was injected into the other side thereof, these sides being symmetric to each other with respect to the backbone of the dorsal skin of the rats. At the time of said injection, 0.5 ml/100 g (body weight) of a 1% dye solution of pontamine sky blue 6B was intravenously injected to the rats, after which the same new plaster and tape were applied to the injected sites for 30 minutes and the rats were then allowed to die by bloodletting. The skin of the dead rats was peeled therefrom and the said serum-injected site of th dorsal skin of the rats was measured for swelling (%) at the edema portion of the skin, dye extravasating area and amount of dye extravasated as in the case of said carrageenin-induced dorsal cutaneous edema in rats (Experiment 1). In each run of the experiment, the treated groups were each compared with the non-treated group by t-inspection.

The results are as shown in Table 7. As is apparent from Table 7, the plaster of Example 24 also exhibited the same significant ($P<0.01$) inhibiting action as the dolenisone tape in this experiment.

TABLE 7

| (Comparison between the plaster of Example 24 and dolenisone tape) | | | | |
|---|---|---|---|---|
| | No. of rats tested | Swelling (%) | Dye extravasating area (cm$^2$) | Amount of dye extravasated (μg) |
| Non-treated group | 12 | 55.5 ± 2.7 | 1.99 ± 0.12 | 23.1 ± 1.3 |
| Plaster (Ex. 24)-treated group | 11 | 26.6 ± 2.1** (52.2) | 0.91 ± 0.06** (54.3) | 12.3 ± 0.8** (46.8) |
| Dolenisone tape-treated group | 11 | 28.0 ± 2.7** (49.6) | 1.00 ± 0.04** (49.7) | 13.4 ± 0.5** (41.9) |

( ): Inhibition ratio to the non-treated group.
**: $P < 0.001$, this indicating there is a significant difference.

EXPERIMENT 5

Effect on picryl chloride-induced ear delayed contact dermatitis in mice

This experiment was carried out in accordance with the method reported by Natsuume et al. This experiment has been considered to be a delayed cellular allergic reaction belonging to IV type allergic reaction called by Gell et al.

Male mice (ICR strain, four weeks old and weighing approximately 30 g each) were shaved at an approximately 2.5 cm × 1.5 cm area of their abdominal skin and, 24 hours later, they were sensitized by the topical reciprocating application of a 7% solution of picryl chloride in a solvent (consisting of acetone and olive oil in a ration by volume of 4 : 1) with a felt roller, 1.3 cm in diameter × 1.7 cm in width. Seven days after the sensitization, both ears of the mice were pinched at the tip portion (0.5 cm long) with a clip fitted with a planar felt, 0.6 cm × 1.0 cm in size, impregnated with a 1% solution of picryl chloride in olive oil, thereby to cause a dermal reaction (first challenge). One hour before, and 16 hours after, the first challenge, the mice were measured for their ear-lobe thickness by the use of a thickness gauge to select those having sufficient edema produced therein. Two days thereafter, the thus selected mice (10 of these mice forming one group) were again induced (second challenge) in the same manner as in the first challenge. One hour later, the plaster (medicinal ingredient content, 4μg; size, 0.7 mm × 1.45 mm) of Example 24 was applied to both the ears of some of the again-induced mice in such a manner that the brim portion of the ear was sandwiched in between the folded plaster to prevent the plaster from peeling from the ear, while a dolenisone tape (the same medicine content and size as above) was applied to both the ears of the remaining again-induced mice in the same manner as indicated above.

The ear-lobes of the mice were measured for thickness one hour before the second challenge and 16 hours thereafter to find an increase in thickness between the two times by the use of a thickness gauge. The data obtained for the treated groups were compared with those obtained for the non-treated group by the t-inspection.

The results are as shown in Table 8.

TABLE 8

| (Comparison between the plaster of Example 24 and dolenisone tape) | | | |
|---|---|---|---|
| | No. of mice tested | Initial thickness of ear-lobe | Increasse in thickness of ear-lobe |
| Non-treated group | 10 | 21.17 ± 0.38 | 11.00 ± 0.74 |
| Plaster (Ex. 24)-treated group | 10 | 20.78 ± 0.45 | 2.86 ± 0.63** (74.0) |
| Dolenisone tape-treated group | 10 | 20.05 ± 0.34 | 3.50 ± 0.87** (68.2) |

( ): Inhibition ratio to the non-treated group.
**: $P < 0.01$, this indicating there is a significant difference.

The plaster of Example 24 exhibited the same performances as the dolenisone tape.

EXPERIMENT 6

Topical anti-inflammatory activity on carrageenin-induced cutaneous edema in rats Male rats of Wistar strain, weighing 95–105 g and being 4 weeks old each, were depilated with Eba Cream (tradename, a depilatory produced by Tokyo Tanabe Pharmaceutical Co., Ltd.) and then treated next day as follows.

A test sample, 2.4×2.4 cm$^2$, of various plasters as shown in Table 9 was applied to a site on one side of the dorsal skin of the rats. Four hours after the application the plaster sample was peeled and 0.1 ml/site of a physiological salt solution containing 1% of carrageenin (Picnin A produced by Pasco International Co.) was soon injected hypodermically into said site, while 0.1 ml/site of a physiological salt solution into a site on the other side, these sites being positioned symmetrically to each other with respect to the backbone of the rats. Two and a half hours later than the injection of the inflammation-causing agent, 0.5 ml/100 g of a 1% solution of pontamine sky blue 6B (a dye produced by Hayashi Pure Chemical Industry Co., Ltd.) in a physiological salt solution were intravenously injected to the rats at the tail, and 30 minutes after this injection, the rats so injected were allowed to die by bloodletting. The skin of the dead rats was peeled therefrom and soon measured for skin thickness at the carrageenin injected site with a dial thickness gauge (pressure 40 g, manufactured by Peacock Co.). The swelling (%) at the edema portion of the skin was calculated as follows.

$$\text{Swelling (\%)} = \frac{\text{Thickness of skin at carrageenin injected site} - \text{Thickness of skin at physiological salt solution injected site}}{\text{Thickness of skin at physiological salt solution injected site}} \times 100$$

Further, the dye extravasating area (cm²) was calculated by multiplying the long diameter by the short diameter in the dye extravasating portion of the skin. Still further, the pontamine sky blue 6B present at this skin portion was extracted by the use of the Harada et al method (Harada, M., Takeuchi, M., Fukao, T. & Katagiri, K.: J. Pharm. Pharmacol., 23, 218, 1971) to find the amount of the extravasating dye by a spectrophotometer.

Formulation of a base and a medicine on a tape-like support is illustrated hereinbelow.

Formulation of a base on a tape-like support

One hundred (100) parts of a styrene-isoprene- styrene TR block copolymer (produced under the trademark of Cariflex TR 1107 by Shell Chemical Co.), 96.93 parts of liquid paraffin (produced under the trademark of Crystol 355 by Esso Standard Oil Co.), 119 parts of a hydrogenated rosin ester (produced under the trademark of Estergum H by Arakawa Chemical Co.) and 51 parts of a rosin-modified maleic resin (produced under the trademark of Malkyd 2-N by Arakawa Chemical Co., Ltd.) were melted in a nitrogen gas stream to obtain a melt. The thus obtained melt (about 150° C.) was cooled to about 120° C., incorporated with 17.3 parts of crotamiton and mixed together to obtain a uniform composition. The composition so obtained was spread to a thickness of 90μ on a releasable paper by the use of a spreader, cooled and covered with a 60μ thick polyethylene film under pressure to transfer the thus spread composition to the film, after which the composition attached film was cut into pieces of a desired size thereby to obtain medicine-free or control plasters.

Formulation of a base containing 3% of a medicinal ingredient on a tape-like support (Preparation of plasters)

One hundred (100) parts of a styrene-isoprene-styrene TR block copolymer (Califlex TR 1107 as defined above), 85.4 parts of liquid paraffin (Crystol 355 as defined above), 119 parts of a hydrogenated rosin (Estergum as defined above) and 51 parts of a rosin-modified maleic resin (Malkyd 2-N as defined above) were melted in a nitrogen gas stream to obtain a melt (about 150° C.) which was cooled to about 120° C., incorporated with a melt in which 11.53 parts of each of the test compositions (medicine content: 3%) shown in Table 9, and then mixed together to obtain a uniform composition. The composition so obtained was spread to a thickness of 90μ on a releasable paper by the use of a spreader, cooled and covered with a 60μ thick polyethylene film under pressure to transfer the thus spread composition to the film, after which the composition attached film was cut into pieces of a desired size thereby to obtain plasters Nos. 1-14.

The results of the experiment are as shown in Table 9.

The preferable thermally and dimensionally stable suports include polypropylene films, polyurethane films, polyester films, non-woven cloths, non-raised cloths, raised cloths, lint paper, polyvinylidene chloride films and polyamide films. The thermally and dimensionally unstable supports include polyethylene films and soft polyvinyl chloride films.

TABLE 9

| Test compound | No. of animal tested | Swelling (%) | Dye extravasating area (cm²) | Amount of dye extravasated (μg) |
| --- | --- | --- | --- | --- |
| Control group (Non-treated) | 7 | 93.4 ± 9.9 | 1.31 ± 0.30 | 20.7 ± 3.9 |
| Plaster (Gel base according to this invention used, but no medicine used) | 7 | 89.0 ± 9.0 [49.7] | 1.25 ± 0.18 [4.5] | 20.1 ± 1.8 [2.9] |
| Plaster No. 1 (3% of Indomethacin contained) | 7 | 61.6 ± 11.6 [34.0] | 0.72 ± 0.23 [45.0] | 12.5 ± 2.8 [39.6] |
| Plaster No. 2 (3% of Flurbiprofen contained) | 7 | 57.8 ± 6.1** [38.1] | 0.57 ± 0.39 [56.5] | 8.5 ± 1.4* [58.9] |
| Plaster No. 3 (3% of Ketoprofen contained) | 7 | 43.1 ± 8.1** [53.9] | 0.21 ± 0.05* [84.0] | 7.2 ± 0.9* [65.0] |
| Plaster No. 4 (3% of Ketoprofen hydroxyethyl ethyl ester contained) | 7 | 66.7 ± 7.2 [28.6] | 0.76 ± 0.17 [42.0] | 13.5 ± 1.2 [34.8] |
| Plaster No. 5 (3% of Ketoprofen glycol ester contained) | 7 | 64.7 ± 8.6* [30.7] | 0.53 ± 0.09* [59.5] | 12.0 ± 1.4 [42.0] |
| Plaster No. 6 (3% of Salocoll contained) | 7 | 69.3 ± 6.1 [25.8] | 0.94 ± 0.25 [28.2] | 14.7 ± 1.8 [29.0] |
| Plaster No. 7 (3% of Voltaren contained) | 7 | 64.9 ± 10.5 [30.5] | 0.78 ± 0.24 [40.5] | 14.4 ± 2.1 [30.4] |
| Plaster No. 8 (3% of Alclofenac contained) | 7 | 68.4 ± 7.0 [26.8] | 0.92 ± 0.26 [29.8] | 14.1 ± 1.2 [31.9] |
| Plaster No. 9 (3% of n-butyl ester of fulfenamic acid contained) | 7 | 74.6 ± 4.5 [20.1] | 0.98 ± 0.21 [25.2] | 15.2 ± 1.5 [26.6] |
| Plaster No. 10 (3% of Oxepinac contained) | 7 | 63.4 ± 8.5* [32.1] | 0.73 ± 0.26 [44.3] | 12.4 ± 1.9 [40.1] |
| Plaster No. 11 Pranoprofen | 7 | 61.4 ± 8.1* [34.3] | 0.74 ± 0.22 [43.5] | 11.1 ± 2.0 [46.4] |

TABLE 9-continued

| Test compound | No. of animal tested | Swelling (%) | Dye extravasating area (cm²) | Amount of dye extravasated (μg) |
|---|---|---|---|---|
| contained) | | | | |
| Plaster No. 12 (3% of Benoxaprofen contained) | 7 | 67.1 ± 9.2 [28.2] | 0.83 ± 0.24 [36.7] | 12.0 ± 1.5 [42.0] |
| Plaster No. 13 (3% of Piroxicam contained) | 7 | 60.5 ± 5.8** [35.2] | 0.58 ± 0.07* [55.7] | 10.3 ± 0.9 [50.3] |
| Plaster No. 14 (3% of Fentiazac contained) | 7 | 63.4 ± 8.7* [32.1] | 0.68 ± 0.19 [48.1] | 11.7 ± 1.1 [43.5] |
| Plaster (Natural rubber used as the gel base, and 3% of Salocoll contained) | 7 | 78.7 ± 3.1 [15.7] | 1.12 ± 0.24 [14.5] | 18.0 ± 3.3 [13.0] |

The asterisks * and ** indicate significant differences from the Control group at P < 0.05 and P < 0.01, respectively.
The values in the parentheses [ ] indicate inhibition ratios with respect to the Control group.

It is seen from the pharmacological test results in Table 9 that the plasters of this invention exhibited very excellent medicinal efficacy as compared with the plaster in which the gel base according to this invention was used but no medicine used and the plaster in which natural rubber was used as the gel base and Salocoll used as the medicine (effective ingredient).

EXPERIMENT 7

An experiment was carried out on 7 subjects who were healthy male adults, 25-39 years old and weighing 50-63 kg each, as mentioned hereinbelow.

Plasters, 1.4 = 1.4 cm each, containing 1% and 3% of each of ketoprofen, indomethacin and flurbiprofen were applied to the subjects at 10 skin sites on the inner sides of both the forearms (5 skin sites on each of the left and right inner sides) and then further fixed to the skin sites with adhesive tapes, respectively. The plasters and adhesive tapes so attached to the skin sites were peeled 0 hour, 4 hours and 8 hours after the application and then inserted into 15 ml test tubes, respectively, after which the test tubes were each incorporated with 5 ml of acetone, shaken lightly and allowed to stand overnight at room temperature. For the tested plasters using therein ketoprofen, indomethacin and flurbiprofen as the medicines (effective ingredients) respectively, 0.5 ml of the supernatant liquid were withdrawn from each of the test tubes and freed of the solvent with nitrogen gas blowing thereinto to obtain a residue which was incorporated with a diazomethane.ether solution for methylation. After the distillation-off of an excess of the diazomethane and ether, the residue so methylated was dissolved in 1 ml of a solution of the internal reference substance in acetone and meansured for absorbability and amount absorbed by means of GC-MF under the conditions as shown in Table 10. The results are as shown in Table 11.

TABLE 10

| | GC-MS condition | | |
|---|---|---|---|
| Sample | Ketoprofen | Indomethacin | Flurbiprofen |
| Instrument: JEOL JMS-D100 Mass spectrometer | | | |
| Ionizing curr. | 300 μA | 300 μA | 300 μA |
| Ionizing volt. | 30 eV | 30 eV | 30 eV |
| Chamber temp. | 200° C. | 200° C. | 200° C. |
| Ion multi. volt. | 1.6 kV | 1.7 kV | 1.48 kV |
| Target ion (1) | m/z: 268 | m/z: 312 | m/z: 244 |
| (2) | m/z: 296 | m/z: 312 | m/z: 258 |
| Internal standard | Ketoprofen-propyl ester | Indomethacin-propyl ester | Triphenyl-methane |
| Instrument: JEOL JGC-20K Gas chromatograph | | | |
| Liq. phase | Silicone-OV-17 | Silicone-OV-1 | Silicone-OV-17 |
| Support | Chromosorb W AW-DMCS | Shimalite W | Chromosorb W AW-DMCS |
| Liq. ph/spt | 2% | 1.5% | 2% |
| Mesh | 60-80 | 80-100 | 60-80 |
| Column temp. | 250° C. | 250° C. | 225° C. |
| Carrier gas press. | He 0.3 kg/cm² | He 0.6 kg/cm² | He 0.3 kg/cm² |
| Column L | 1 m | 1 m | 1 m |

The absorbency and amount absorbed were calculated from the following formulae:

$$\text{Absorbency (\%)} = \left\{ 1 - \frac{\text{Amount of medicine remaining 4 or 8 hours after administration}}{\text{Amount of medicine originally administered (0 hour after administration)}} \right\} \times 100$$

$$\text{Amount of medicine absorbed (μg)} = \left( \begin{array}{l} \text{Amount of medicine originally administered (0 hour after administration)} - \text{Amount of medicine remaining 4 or 8 hours after administration} \end{array} \right)$$

TABLE 11

Percutaneous absorption of three drugs in men after topical application of plasters

| | Time after application | | | |
|---|---|---|---|---|
| | 4 hr | 8 hr | 4 hr | 8 hr |
| | Percent absorption (%) | | Amount absorption (μg) | |
| Ketoprofen | | | | |
| 1% | 16.77 ± 2.33 | 19.98 ± 2.38 | 30.81 ± 4.29 | 36.71 ± 4.37 |
| 3% | 9.56 ± 3.25 | 13.96 ± 3.19 | 41.55 ± 14.12 | 60.61 ± 13.85 |
| Indomethacin | | | | |
| 1% | 1.27 ± 3.25 | 2.71 ± 0.64 | 2.30 ± 1.83 | 4.92 ± 1.16 |
| 3% | 3.52 ± 1.14 | 4.28 ± 0.45 | 16.67 ± 5.41 | 20.21 ± 2.13 |
| Flurbiprofen | | | | |
| 1% | 5.53 ± 1.71 | 6.54 ± 0.99 | 9.05 ± 2.80 | 10.70 ± 1.61 |
| 3% | 6.98 ± 0.31 | 8.40 ± 1.17 | 41.19 ± 1.82 | 49.56 ± 6.92 |

Each skin was treated with containing 1% and 3% of drugs per 1.4 × 1.4 cm of plasters (adhesive mass: 90 g/m²).
The treated skin was covered by tape.
Each value represents mean ± S.E. of four to five subjects.

It is seen from the pharmacological experiment results in the above Table that the plasters of this invention were very excellent in discharging the medicine therefrom.

EXPERIMENT 8

Percutaneous absorption of etofenamate from etofenamate plaster in men

[Materials]

Etofenamate plasters respectively containing 5, 10, 12.5 and 15% and placebo plasters were prepared. Each plaster was 1.4 ×1.4 cm in size.

[Methods]

An experiment was carried out on five healthy male volunteers. The etofenamate plasters and placebo plasters were applied to the skin of both the forearms (FIG. 1A) and were fixed to the skin with adhesive tapes.

Some of the plasters were removed 4 hours after the application and the other were removed 8 hours after the application, after which these plasters so removed were placed in 25 ml measuring flasks, respectively.

For washing the plaster on the skin surface at the applied site, the funnel was put on the applied site and then a small quantity of methyl alcohol was poured thereto several times through the leg of the funnel (FIG. 2) to extract the medicine (etofenamate) from the plaster (FIG. 1B).

The extract so obtained was also placed in the 25 ml measuring flask and incorporated with methyl alcohol to the extent that the total solution reached accurately 25 ml in the flask. This solution was used as a sample solution. Optical density of the sample solution was measured at 287 nm by a double beam spectrophotometer.

Etofenamate concentrations were determined by comparison with etofenamate standards.

Absorption rate of etofenamate was calculated by the following equation:

Absorption rate of etofenamate (%) =

$$100 \times \left(1 - \frac{\text{Amount of etofenamate [I]}}{\text{Amount of etofenamate [II]}}\right)$$

Amount of etofenamate [I] =

Amount of etofenamate recovered from the plaster either 4 or 8 hours after application Amount of etofenamate [II] =

Amount of etofenamate in the plaster used for application

TABLE 12

Percutaneous absorption of Etofenamate in men after topical application of Rheumon plasters

| | Time after application | | | |
|---|---|---|---|---|
| | 4 hr | 8 hr | 4 hr | 8 hr |
| Plaster | Percent absorption (%) | | Amount absorption (μg) | |
| Etofenamate 5% | 1.6 ± 0.4 | 4.8 ± 0.3 | 14.5 ± 3.5 | 43.4 ± 2.5 |
| Etofenamate 10% | 9.9 ± 1.1 | 10.7 ± 1.0 | 198.0 ± 21.5 | 215.0 ± 19.9 |
| Etofenamate 12.5% | 6.4% ± 1.5 | 11.0 ± 2.0 | 158.5 ± 37.1 | 273.0 ± 50.7 |
| Etofenamate 15% | 13.9 ± 2.1 | 16.8 ± 2.0 | 387.0 ± 59.2 | 468.5 ± 55.9 |

Each value represents mean S.E. of five subjects.

It is seen from the results of the above percutaneous absorption experiments that the plasters of this invention are excellent in discharging the medicine therefrom and in medicinal efficacy.

EXPERIMENT 9

Comparison of percutaneous absorption between plasters of this invention and Secours 1. Materials to be tested Plasters [effective ingredient, Salocoll; base, synthetic tube, rubber (SIS)] of Example 17 and Secours [effective ingredient, Salocoll; base, natural rubber plus synthetic rubber] were used as two samples. The plasters of these two types were each cut into pieces, 2 ×2 cm in size, having a Salocoll content of 2 mg/2×2 cm.

2. Method of application

Twelve of the thus obtained plaster pieces (6 pieces of each of the two different type plasters) were applied to 7 healthy male subjects on the dorsal skin, and pairs of the different type plaster pieces were peeled and recovered from the skin 0, one, two 4, 8 and 24 hours after the application, respectively.

3. Preparation of specimens

The plaster pieces so recovered were each placed in a test tube (1.4 ×12.5 cm) provided with a screw cap, incorporated with 5 ml of a mixture of ethanol and methanol in a ratio of 1:2, sealed up in the tube, heated to 70–80° C. using a water bath for 2 hours and then subjected to Sclocoll extraction. Four milliliters (4 ml) of the resulting Salocoll solution were evaporated to dryness to obtain a residue which was incorporated with 150 μ l of acetone to prepare a solution of the residue in the acetone, the solution being for use as a specimen for gas chromatography.

4. Gas chromatography

Using Yanagimoto G80 Model and a glass column, gas chromatography using Yanagimoto G80 Model and a glass column, 1.5 m ×3 mm, filled up with XE-60 1% chromosorb W (60-80 mesh), the specimens so prepared were subjected to gas chromatography under the following conditions:

Carrier gas: $N_2$, 50 ml/min.
Temperature at the inlet: 250° C.
Temperature of the column: 170° C.

The determination of amount of Salocoll contained in the specimens was effected using an amount-measuring curve drawn on the basis of ratios of height of peaks between the standard Salocoll and the inner standard substance (disphenylamine).

5. Results

Assuming that the amount of Salocoll remaining 0 hour after the application (the amount being the original one) is expressed by 100%, the absorbability of Salocoll was calculated from the following equation:

$$\text{Absorbability (\%)} = \left(1 - \frac{\text{Amount of Salocoll remaining each predetermined time length after application}}{\text{Amount of Salocoll applied}}\right) \times 100$$

The absorbabilities are as shown in Table 14 and FIG. 3.

The Table and FIG. 3 show that there were not appreciable differences in absorbability between the plaster of Example 17 and the Secours until 2 hours after the application, there were significant differences therebetween until 4–24 hours after the application and the absorbability of the plaster of Example 17 was twice as high as that of the Secours 8 hours after the application. It is clearly seen from the above that the plaster of Example 17 has excellent absorbability as compared with the Secours.

6. Observations

It was investigated what effects the rubber bases would have on the absorbability of the medicine contained therein and, as a result of the investigation, it was found that the base composed only of the synthetic rubber enabled the medicine to be satisfactorily absorbed, while that composed of the natural rubber and synthetic rubber in admixture allowed the medicine to be unsatisfactorily absorbed.

The constant of velocity of vanishment of Salocoll from the rubber base (that is, the absorption velocity constant) until 8 hours after the application is as shown in the following Table 13.

TABLE 13

| | Vanishing velocity constant (Absorption velocity constant) |
|---|---|
| Plaster of Example 17 | 0.1179 hr$^{-1}$ |
| Secours | 0.0463 hr$^{-1}$ |

The constant of the plaster of Example 17 was 2.5-3 times as high as that of the Secours.

TABLE 14

Effect of adhesive mass (base) in percutaneous absorption

| | Absorption of salocoll 8% | | | | |
|---|---|---|---|---|---|
| | 1 hr | 2 hr | 4 hr | 8 hr | 24 hr |
| plaster (Ex. 17) treated group | 5.6 ± 2.1 | 8.3 ± 2.1 | 31.2 ± 4.2 | 59.7 ± 2.8 | 94.4 ± 1.4 |
| SECOURS treated group | 4.3 ± 2.6 | 10.3 ± 3.4 | 18.9 ± 2.6* | 30.8 ± 1.7 | 68.4 ± 1.7 | applied dose 2mg Salocoll/2 × 2cm/man, mean ± SE
*: $p < 0.05$,
**: $p < 0.01$, n = 7

EXPERIMENT 10

Test for comparison of stability between natural rubber (NR) and a styrene-isoprene-styrene TR block copolymer and Test for usability of these bases for plasters.

(1) Plasters A (SIS used as the base)

One hundred (100) parts of a styrene-isoprene-styrene TR block copolymer (Califlex TR-1107 as previously defined), 200 parts of liquid paraffin (Crystol 355 as previously defined) and 100 parts of a hydrogenated ester (Estergum H as previously defined) were melted in a nitrogen gas stream. The resulting melt was incorporated with 5.5% of l-menthol, 3.7% of glycol salicylate and 1.6% of dl-camphor and mixed together thereby to obtain a uniform composition (the above percentages being based on the weight of said melt). A portion of the thus obtained composition was poured into a metallic mold, 2 mm in thickness and 19 mm in diameter, and then cooled thereby to obtain circular sheet-like samples (1), while the remainder thereof was spread to a depth of about 200 μ on a raised cloth by the use of a spreader and covered on the surface with a polypropylene film to obtain film-supported plasters A.

(2) Plasters B (NR used as the base)

One hundred (100) parts of natural rubber (RSS No. 1), 33 parts of polybutene (HV-300, produced by Nippon Oil Co.) and 58 parts of a hydrogenated rosin ester (Estergum H as previously defined) were mixed together by the use of a mixer. The resulting mixture was incorporated with 5.5% of l-menthol, 3.7% of glycol salicylate and 1.6% of dl-camphor and then mixed together thereby to obtain a uniform composition (the above percentages being based on the weight of said melt). A portion of the thus obtained composition was poured into the same metallic mold as mentioned above thereby to obtain circular sheet-like samples (2), while the ramaining portion thereof was spread to a depth of about 200 μ on a raised cloth by the use of a spreader and covered on the surface with a polypropylene film thereby to obtain film-supported plasters B.

A comparative test was made on the circular sheet-like samples (1) and (2) to find their stability against their fluidity with the lapse of time. The results of the comparative test are as indicated in Tables 15A, 15B and FIG. 4.

More particularly, the test was made by placing the samples in receptacles of a predetermined capacity, placing the receptacles in thermo-hygrostats (PL-3 Model produced by Tabai Works) which were maintained at a humidity of 80% at temperatures of 30, 40 and 50° C. respectively, and closing the thermo-hygrostats with lids to allow the receptacles to stand under the same temperature and humid conditions as above thereby investigating the dimensional changes of the samples from their original sizes with the lapse of time (1 to 35 days). As is clear from the results as shown in Tables 15A, 15B and FIG. 4, the SIS base is low in fluidity and high in stability as compared with the NR base.

TABLE 15A

| | | Initial | 1 day later | 3 days later | 7 days later | 10 days later | 17 days later | 35 days later |
|---|---|---|---|---|---|---|---|---|
| 30° C. | NR | 0 | 1.0 mm | 1.5 mm | 3.0 mm | 4.0 mm | 5.0 mm | 6.4 mm |
| | SIS | 0 | 0.5 | 1.0 | 1.0 | 1.0 | 1.0 | 1.6 |
| 40° C. | NR | 0 | 2.0 | 3.0 | 5.0 | 5.5 | 6.5 | 9.3 |
| | SIS | 0 | 1.5 | 2.5 | 3.5 | 3.5 | 4.0 | 4.9 |
| 50° C. | NR | 0 | 3.0 | 5.5 | 7.5 | 8.5 | 11.0 | 14.0 |
| | SIS | 0 | 4.5 | 7.0 | 7.5 | 8.0 | 8.0 | 8.0 |

*Formulation

TABLE 15B

| | NR base | SIS base |
|---|---|---|
| NR (RSS #1) | 44.90% | — % |
| SIS (TR-1107) | — | 21.44 |
| Estergum H | 26.04 | 21.44 |
| Polybutene (HV-300) | 14.82 | |
| Liquid paraffin (-355) | — | 42.88 |
| Medicine  l-menthol | 5.54 | 5.54 |
| Salocoll | 3.68 | 3.68 |
| dl-camphor | 1.59 | 1.59 |
| PB (P-70) | 1.85 | 1.85 |
| BHT | 0.78 | 0.78 |
| Flavor | 0.80 | 0.80 |
| | 100 | 100 |

Conventional plasters are very disadvantageous in that they will give a pain when peeled after their application. In order to substantiate that plasters comprising a SIS base will give a much less pain than those comprising a NR base, the plasters A and the plasters B were respectively tested for three properties (tackiness, adhesiveness and attachability) by the same method of evaluating plasters as heretofore used. The results are as shown in Table 16. Further, the plasters A and B were applied to human subjects to find their attachability and the degree of pains they would give to the subjects when peeled with the results being as shown in Table 17.

(1) Results of test for properties

TABLE 16

|  | (*1) 180° peel adhesive strength test | (*2) J-DOW tack strength test | (*3) PROUGTACK attachment strength test |
|---|---|---|---|
| Plaster comprising conventional NR base [Plaster B] | 450 (±50) | No 31 | 350 (±50) |
| Plaster comprising SIS base [Plaster A] | 650 (±50) | No 31 | 350 (±50) |

(*1) 180° peel type adhesive strength test: A Bakelite board was used as the material to be adhered to in this test. Each of the test pieces, 18 mm wide each, obtained respectively from the plasters A and B was applied to the Bakelite board under a load of 850 g by the use of rubber rollers, allowed to stand in a test room for at least 60 minutes and then tested for peel adhesive strength at a pull speed of 300 mm/min. by the use of an Instron type tensiometer.
(*2) J-DOW type tack test: There were provided 32 steel balls respectively having diameters ranging fron No 1 to No 32, No 1 corresponding to 1/32 inch, No 32 corresponding to 32/32 inch, that is one inch, and No X + 1 being 1/32 inch larger than No X wherein X is an integer of from 1 to 29. There was further provided a slope inclined at an angle of 30° with respect to the horizontal plane, to the surface of which was applied a 10 cm long test piece of each of the plasters A and B with its propylene film side facing to the surface of the slope. Each steel ball was allowed to start to roll down on the slope surface at the point 10 cm upward from the near end of the test piece so applied. The tack strength was expressed by the No (diameter) of the steel ball which stopped rolling with the 10 cm long test piece. The larger the No is, the higher the tack strength expressed is.
(*3) Probe tack type attachment strength test: Each of the plasters A and B was placed on a Bakelite board with its film-free side facing thereto. A weight was contacted with the film-covered side of each of the plasters A and B under a load of 100 g for 10 seconds, the weight having previously been so adjusted that the contact area between the weight and plaster would be a 5 mm-diameter circle when contacted with the plaster, after which the plaster was tested for attachment strength by peeling from the Bakelite board at a pull speed of 300 mm/min, by the use of an Instron type tensiometer.

(2) Results of test for application

The plasters A and B were applied to 50 subjects (25 males and 25 females) at the left and right forearms, respectively to investigate the following items:
a. Attachability, that is, durability of adhesion of applied plasters to the skin (State of applied plasters 8 hours after application) and
b. Degree of pain given when plaster peeled.
The results are as shown in Table 17.

TABLE 17

|  | (*a) Attachability | (*b) Degree of pain given when plaster peeled |
|---|---|---|
| Plaster B comprising conventional NR base | 0.91 | 0.43 |
| Plaster A comprising SIS base | 0.90 | 0.61 |

The values for attachability and degree of pain in Table 17 are mean values obtained as follows.

The subjects were requested to report on the state of the applied plasters and degree of pain given by peeling 8 hours after the application. The states and degrees of pain so reported were expressed respectively by numeral values as indicated below:

| (*a) Attachability of applied plaster | |
|---|---|
| Numeral value | State reported |
| 0.2 | Entirely peeled |
| 0.4 | Approximately half peeled |
| 0.6 | Approximately one-third peeled |
| 0.8 | Slightly peeled at the end portion |
| 1.0 | Not peeled at all |
| (*b) Degree of pain given when peeled (8 hours after the application) | |
| Numeral value | Degree of pain reported |
| 0.2 | Feel severe pain |
| 0.4 | Feel pain |
| 0.6 | Feel slight pain |
| 0.8 | Feel substantially no pain |
| 1.0 | Feel no pain |

The mean values in Table 17 were calculated from the following equation.

$$\text{Average value} = \frac{\text{Total of numeral values derived from reports of subjects}}{\text{No. of subjects}}$$

It can be said that plasters exhibiting a higher numeral value are more satisfactory.

It has been found from the above that the plaster A comprising the SIS base is satisfactorily attachable while it will give no pain when peeled. These desirable properties are those which have been sought in the conventional plasters.

It is seen from the foregoing results that as compared with conventional plasters comprising a NR base, plasters comprising such a SIS base are very advantageous in that they have low fluidity and satisfactory attachability and will give a much alleviated pain when peeled.

EXPERIMENT 11

Patch test on healthy male subjects

Patches (1.4×1.4 cm in size) cut from the previously mentioned plasters Nos. 1–6, 10–12 and 14 (see Tables 9 and 19) comprising the SIS base and 3% of any one medicinal ingredient selected from ketoprofen, ketoprofen ethyl ester, ketoprofen hydroxyethyl ester, flurbiprofen, indomethacin, oxpinac, fentiazac, voltaren, pranoprofen, benoxaprofen and Salocoll, as well as patches (1.4×1.4 cm in size) cut from the previously mentioned plaster (see Tables 9 and 19) comprising the NR base and 3% of Salocoll, were applied respectively to 30 healthy male subjects at 10 sites on the skin of the inner side of the forearms and allowed to stand on the skin for 24 hours. The plasters so left applied were peeled and the skin portions from which the plasters had been peeled were visually examined in accordance with the following criteria (Table 18) 30 minutes and 24 hours after the peeling.

TABLE 18

| Score | Reaction of skin portions |
|---|---|
| − | No anomalous reactions appreciated |
| ± | Slight erythema |
| + | Erythema or papule |
| ++ | Erythema and swelling. Or erythema and papule |
| +++ | Erythema, swelling and small vesicle. Or erythema, swelling and papule |
| ++++ | Bulla, erosion |

TABLE 19

| Plaster tested | Results of examination Positivity (%) on the assumption that the score "±" or worse in Table 18 is positive. | |
|---|---|---|
| | 30 minutes after peeling | 24 hours after peeling |
| Plaster No. 1 (3% of indomethacin contained) | 0 (0/30) | 0 (0/30) |
| Plaster No. 2 (3% of flurbiprofen contained) | 0 (0/30) | 0 (0/30) |
| Plaster No. 3 (3% of ketoprofen contained) | 0 (0/30) | 0 (0/30) |
| Plaster No. 4 (3% of ketoprofen ethyl ester contained) | 0 (0/30) | 0 (0/30) |
| Plaster No. 5 (3% of ketoprofen hydroxylethyl ester contained) | 0 (0/30) | 0 (0/30) |
| Plaster No. 6 (3% of Salocoll contained) | 0 (0/30) | 0 (0/30) |
| Plaster No. 10 (3% of oxepinac contained) | 3.3 (1/30) | 0 (0/30) |
| Plaster No. 11 (3% of pranoprofen contained) | 3.3 (1/30) | 0 (0/30) |
| Plaster No. 12 (3% of benoxaprofen contained) | 3.3 (1/30) | 0 (0/30) |
| Plaster No. 14 (3% of fentiazac contained) | 0 (0/30) | 0 (0/30) |
| Plaster comprising the NR base (3% of Salocoll contained) | 26.6 (8/30) | 20 (6/30) |

It is clearly seen from the results in Table 19 that the plasters Nos. 1–6, 10–12 and 14 comprising the SIS base are advantageous over the plaster comprising the NR base in that the former were less irritative to the skin and caused less eruption thereon.

What is claimed is:

1. A plaster containing a composition comprising by weight, 100 parts of a thermoplastic elastomer selected from the group consisting of styrene-isoprene-styrene block copolymers, styrene-isoprene-styrene radial block copolymers, styrene-butadiene-styrene block copolymers, styrene-butadiene-styrene radial block copolymers and mixtures thereof, 25–370 parts of a member selected from the group consisting of oils and high fatty acids which are a solvent for the diolefinic block, not for the monoolefinic block, to provide gel-like properties to said plaster, 25–200 parts of a tack-providing resin and 0.09–110 parts of a medicinal ingredient uniformly distributed in said plaster.

2. A plaster prepared by:
dissolving (1) 100 parts by weight of at least one thermoplastic elastomer selected from the group consisting of styrene-isoprene-styrene block copolymers, styrene-isoprene-styrene radial block copolymers, styrene-butadiene-styrene block copolymers, styrene-butadiene-styrene radial block copolymers and mixtures thereof and (2) 25–100 parts by weight of a tack providing resin in (3) 25–370 parts by weight of a member selected from the group consisting of oils and higher fatty acids which are a solvent for the diolefinic block, not for the monoolefinic block,
incorporating the resulting solution with 0.09–110 parts by weight of a medicinal ingredient to obtain a uniform composition,
spreading the thus obtained composition directly on a support, and then
covering the support-carried composition with a releasable material.

3. A plaster prepared by:
dissolving 100 parts by weight of at least one thermoplastic elastomer selected from the group consisting of styrene-isoprene-styrene block copolymers, styrene-isoprene-styrene radial block copolymers, styrene-butadiene-styrene block copolymers, styrene-butadiene-styrene radial block copolymers and mixtures thereof and (2) 25–100 parts by weight of a tack providing resin in (3) 25–370 parts by weight of a member selected from the group consisting of oils and higher fatty acids, which are a solvent for the diolefinic block, not for the monoolefinic block,
incorporating the resulting solution with 0.09–110 parts by weight of a medicinal ingredient to obtain a uniform composition,
spreading the thus obtained composition on a thermally and dimensionally stable support,
pressing a thermally and dimensionally unstable support onto the composition-spread stable support, and then
covering the composition layer carried on the unstable support with a releasable material.

4. A plaster according to claim 2, wherein the support is a member selected from the group consisting of cloths, non-woven cloths, non-raised cloths, raised cloths, lint paper, polyester films, poly-vinylidene chloride films, polypropylene films, polyurethane films and polyamide films.

5. A plaster according to claim 3, wherein the stable support is a member selected from the group consisting of cloths, non-woven cloths, non-raised cloths, raised cloths, lint paper, polyester films, polyvinylidene chloride films, polypropylene films, polyurethane films and polyamide films, and the unstable support is a member selected from the group consisting of polyethylene films and polyvinyl chloride films.

6. A plaster according to claim 1, 2 or 3, wherein the oil or higher fatty acid is a member selected from the group consisting of almond oil, olive oil, camellia oil, persic oil, peanut oil, sesame oil, soybean oil, mink oil, cotton seed oil, corn oil, safflower oil, coconut oil, castor oil, oleic acid and liquid paraffin.

7. A plaster according to claim 1, 2 or 3, wherein the tack-providing resin is a member selected from the group consisting of rosin, dehydrogenated rosin, glycerine esters of dehydrogenated rosin, glycerine esters of gum rosin, hydrogenated rosin, glycerine esters of hydrogenated rosin, pentaerithritol esters of hydrogenated rosin, methyl esters of hydrogenated rosin, polymerized rosin, glycerine esters of polymerized rosin, coumarone-indene resins, hydrogenated petroleum resins, maleic anhydride-modified rosin and rosin derivatives, $C_5$ petroleum resins and half esters of styrene-maleic acid copolymers.

8. A plaster according to claim 1, 2 or 3, wherein the medicinal ingredient is a member selected from the group consisting of methyl salicylate, glycol salicylate, salicylic acid, menthol, peppermint oil, camphor, thymol, acrinol, scopolic extract, chlorpheniramine maleate, diphenhydramine, benzyl nicotinate, capsicum extract, nonyl vanillylamide, capsaicin, ibuprofen, indomethacin, alclofenac, ketoprofen, flurbiprofen, fenoprofen, flufenamic acid, niflumic acid, indoprofen, diclofenac sodium, naproxen, clidanac, tolmetin, suprofen, bendazac, oxepinac, pranoprofen, benoxaprofen, piroxicam, fentiazac, Fentiazac esters thereof and corticosteroids.

9. A plaster according to claim 1, 2 or 3, wherein the medicinal ingredient is etofenamate.

10. A process for the preparation of a plaster which comprises:
dissolving (1) 100 parts by weight of at least one thermoplastic elastomer selected from the group consisting of styrene-isoprene-styrene block copolymers, styrene-isoprene-styrene radial block copolymers, styrene-butadiene-styrene block copolymers, styrene-butadiene-styrene radial block copolymers and mixtures thereof, and (2) 25–100 parts by weight of a tack-providing resin in (3) 25–370 parts by weight of a member selected from the group consisting of oils and higher fatty acids which are a solvent for the diolefinic block, not for the monoolefinic block,
incorporating the resulting solution with 0.09–110 parts by weight of a medicinal ingredient to obtain a uniform composition,
spreading the thus obtained composition directly on a support, and then
covering the support-carried composition with a releasabel material.

11. A process for the preparation of a plaster which comprises:
dissolving (1) 100 parts by weight of at least one thermoplastic elastomer selected from the group consisting of styrene-isoprene-styrene block copolymers, styrene-isoprene-styrene radial block copolymers, styrene-butadiene-styrene block copolymers, styrene-butadiene-styrene radial block copolymers and mixtures thereof, and (2) 25–100 parts by weight of a tack-providing resin in (3) 25–370 parts by weight of a member selected from the group consisting of oils and higher fatty acids which are a solvent for the diolefinic block, not for the monoolefinic block,
incorporating the resulting solution with 0.09–110 parts by weight of a medicinal ingredient to obtain a uniform composition,
spreading the thus obtained composition on thermally and dimensionally stable support,
pressing a thermally and dimensionally unstable support onto the composition-spread stable support to transfer the composition layer therefrom to the unstable support, and then
covering the composition carried on the unstable support with a releaseable material.

* * * * *